United States Patent
Schoch McGovern et al.

(10) Patent No.: US 11,644,463 B2
(45) Date of Patent: May 9, 2023

(54) DETECTION OF AN AUTOANTIBODY

(71) Applicant: EUROIMMUN Medizinische Labordiagnostika AG, Luebeck (DE)

(72) Inventors: Susanne Schoch McGovern, Bonn (DE); Albert Becker, Bonn (DE)

(73) Assignee: Euroimmun Medizinische Labordiagnostika AG, Luebeck (DE)

( * ) Notice: Subject to any disclaimer, the term of this patent is extended or adjusted under 35 U.S.C. 154(b) by 42 days.

(21) Appl. No.: 16/947,631

(22) Filed: Aug. 11, 2020

(65) Prior Publication Data
US 2021/0063393 A1 Mar. 4, 2021

(30) Foreign Application Priority Data
Aug. 30, 2019 (EP) .................................... 19194680

(51) Int. Cl.
*G01N 33/564* (2006.01)
*C07K 14/47* (2006.01)

(52) U.S. Cl.
CPC ....... *G01N 33/564* (2013.01); *C07K 14/4705* (2013.01); *G01N 2800/24* (2013.01); *G01N 2800/28* (2013.01); *G01N 2800/2857* (2013.01)

(58) Field of Classification Search
CPC ............. G01N 33/564; G01N 2800/24; G01N 2800/28; G01N 2800/2857; C07K 14/4705
See application file for complete search history.

(56) References Cited

U.S. PATENT DOCUMENTS 10,041,959 B2 * 8/2018 Wang ................... G01N 33/564
2008/0254482 A1 * 10/2008 Mattoon ................. A61P 37/06
435/7.1

FOREIGN PATENT DOCUMENTS

| CN | 109490527 | 3/2019 | |
| EP | 1 309 613 | 5/2003 | |
| EP | 2 483 417 | 8/2012 | |
| WO | 02/12269 | 2/2002 | |
| WO | 2011/041433 | 4/2011 | |
| WO | WO-2011142900 A1 * | 11/2011 | ......... G01N 33/6896 |
| WO | 2012/125805 | 9/2012 | |
| WO | 2013/151665 | 10/2013 | |

OTHER PUBLICATIONS

Extended Search Report dated Mar. 4, 2020 in European Application No. 19194680.5, 13 pages.
Bastien Joubert, 3rd Congress of the European Academy of Neurology; 2017, pp. 1-18, XP055670965.
Jung et al., Journal of Neurochemistry; 2015, 134: 327-339.
Wandinger et al., Deutsches Ärzteblatt International (online); 2018, 115:666-673, 12 pages.

* cited by examiner

*Primary Examiner* — Kimberly Ballard
(74) *Attorney, Agent, or Firm* — Grüneberg and Myers PLLC

(57) ABSTRACT

A diagnostically useful carrier includes a peptide including the amino acid sequence set forth in SEQ ID NO: 1, SEQ ID NO: 2, SEQ ID NO: 3, SEQ ID NO: 4 or a variant thereof. A kit, a composition, a detection method, use for detecting a neurological disease, a human autoantibody specifically binding to Drebrin and a therapeutic compound or combination for use in the treatment of a neurological use are also useful.

7 Claims, 9 Drawing Sheets
Specification includes a Sequence Listing.

| Pat. | age | sex | binding pattern | HEp 2 | CSF | EEG | additional diagnosis | symptoms | time point | MRI |
|---|---|---|---|---|---|---|---|---|---|---|
| #1 | 50 | m | neuropil | neg | ↑ protein levels | slowing L temp | CGL (FD: 2017), asthma medication: Fluticasonfuroat/ Vilanterol | memory impairment, status epilepticus | 07/2016 | swelling hip bilat |
| | | | | | | | | | 01/2017 | ↓ V hip R |
| | | | | | | | | | 07/2017 | swelling hip R |
| #2 | 38 | f | - | ANA | ↑ protein levels | focus R temp | episodes of night sweats (FD:2015) | unaware focal seizures | 05/2015 | swelling hip + amy R constant |
| | | | | | | | | | 08/2015 | constant |
| | | | | | | | | | 04/2016 | constant |
| #3 | 68 | f | neuropil | neg | ↑ protein levels | focus L temp | polymyalgia rheumatica (FD: 2012), medication: MTX, Pred. | unaware focal seizures; bradycardia | 06/2015 | swelling amy L |
| | | | | | | | | | 11/2016 | constant |
| #4 | 23 | f | - | neg | ↑ protein levels, pleoc. | focus L temp | selective IgA deficiency, numbness and paresis of right hand, visual field loss right | unaware focal/ bilat tonic-clonic seizures; epilepsia partialis continua | 07/2002 | normal |
| | | | | | | | | | 08/2006 | gliosis hem L |
| | | | | | | | | | 09/2012 | gliosis hem L |
| | | | | | | | | | 08/2013 | constant |
| | | | | | | | | | 08/2016 | progressive |
| | | | | | | | | | 02/2017 | constant |
| | | | | | | | | | 08/2017 | constant |
| | | | | | | | | | 01/2018 | constant |

FIG. 1

| Pat. | time-point | AED | IS | MRI | AB status | IQ | Exec. Mem. | Verb. Mem. | Fig. Mem. | BDI |
|---|---|---|---|---|---|---|---|---|---|---|
| #1 | 07/16 | Val (1200) | | R hip ↑ | 1:5000 (s) 1:1 (csf) | | +++ | ++++ | +++ | 0 | +++ |
| | 01/17 | Lam (250) | | R hip ↓ | negative | | | ++++ | ++ | 0 | +++ |
| | 07/18 | Lam (400) | | R hip ↑ | negative | +++ | ++++ | +++ | 0 | +++ |
| #2 | 08/15 | Lev (1500) | | R amy ↑ | 1:2500 (s) 1:100 (csf) | +++ | +++ | ++++ | +++ | +++ |
| | 03/16 | Lam (400) | | R amy ↑ | 1:2500 (s) | | +++ | ++++ | +++ | +++ |
| | 03/17 | Lam (400) | | | | +++ | ++ | ++++ | +++ | +++ |
| #3 | 06/15 | Lev (2000) | Pred. p. & Pred. (2.5) | L amy ↑ (09/15) | 1:10000 (s) negative (csf) | +++ | +++ | +++ | +++ | +++ |
| | 12/15 | Lev (2000) | Pred. (2.5) | L amy ↑ | | | +++ | +++ | +++ | +++ |
| | 11/16 | Lev (3000), Lac (200) | Pred. (2.5) | | negative (s) negative (csf) | | +++ | ++ | + | +++ |
| #4 | 02/13 | Lev (3000), Oxc (300) | | L hemis ↓ (06/13) | 1:5000 (s') 1:10 (csf') | +++ | 0 | 0 | + | |
| | 07/16 | Lev (4000) | Pred. p. | L par ↑, temp-pol ↑ | 1:1000 (s) negative (csf) | +++ | 0 | + | + | +++ |
| | 02/17 | Lev (4000), Clob (50), Zon (600) | Pred. p. | L hemis ↓ | | | 0 | + | + | +++ |
| | 08/17 | Lev (4000) | Pred. p. | no further dynamic | | | + | +++ | + | +++ |
| | 04/19 | Lev (4000), Clob (50), Zon (600) | | L hemis ↓ | | | 0 | +++ | +++ | +++ |

FIG. 2

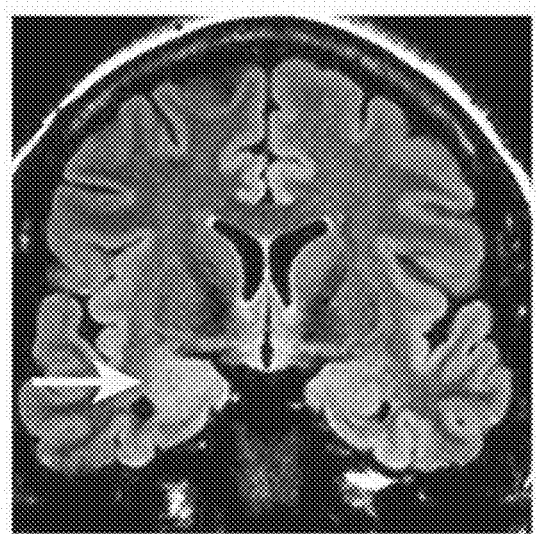 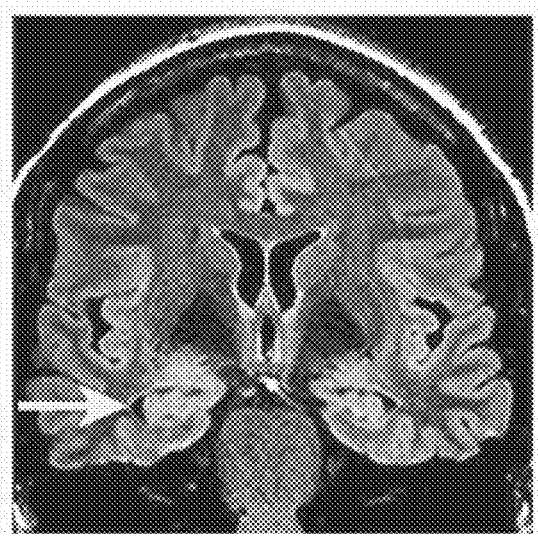
FIG. 3A　　　　　　　　FIG. 3B
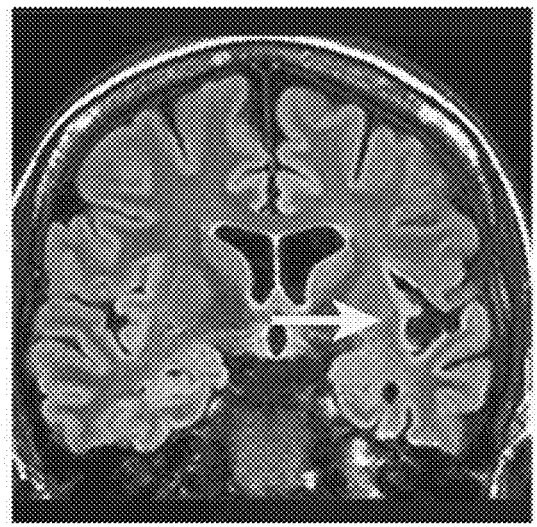 
FIG. 3C　　　　　　　　FIG. 3D

SEQUENCE LISTING

<160> NUMBER OF SEQ ID NOS: 4

<210> SEQ ID NO 1
<211> LENGTH: 126
<212> TYPE: PRT
<213> ORGANISM: Artificial Sequence
<220> FEATURE:
<223> OTHER INFORMATION: Fragment of human Drebrin

<400> SEQUENCE: 1

Gly Ser His Leu Asp Ser His Arg Arg Met Ala Pro Thr Pro Ile Pro
1               5                   10                  15

Thr Arg Ser Pro Ser Asp Ser Ser Thr Ala Ser Thr Pro Val Ala Glu
            20                  25                  30

Gln Ile Glu Arg Ala Leu Asp Glu Val Thr Ser Ser Gln Pro Pro Pro
        35                  40                  45

Leu Pro Pro Pro Pro Pro Ala Gln Glu Thr Gln Glu Pro Ser Pro
    50                  55                  60

Ile Leu Asp Ser Glu Glu Thr Arg Ala Ala Pro Gln Ala Trp Ala
65                  70                  75                  80

```
Gly Pro Met Glu Glu Pro Pro Gln Ala Gln Ala Pro Pro Arg Gly Pro
                 85                  90                  95

Gly Ser Pro Ala Glu Asp Leu Met Phe Met Glu Ser Ala Glu Gln Ala
            100                 105                 110

Val Leu Ala Ala Pro Val Glu Pro Ala Thr Ala Asp Ala Thr
        115                 120                 125

<210> SEQ ID NO 2
<211> LENGTH: 114
<212> TYPE: PRT
<213> ORGANISM: Artificial Sequence
<220> FEATURE:
<223> OTHER INFORMATION: Fragment of human Drebrin

<400> SEQUENCE: 2

Leu Pro Glu Pro Pro Ala Thr Phe Cys Asp Pro Glu Glu Val Glu Gly
1               5                  10                  15

Glu Ser Leu Ala Ala Pro Gln Thr Pro Thr Leu Pro Ser Ala Leu Glu
            20                  25                  30

Glu Leu Glu Gln Glu Gln Glu Pro Glu Pro His Leu Leu Thr Asn Gly
        35                  40                  45

Glu Thr Thr Gln Lys Gly Thr Gln Ala Ser Glu Gly Tyr Phe Ser
    50                  55                  60

Gln Ser Gln Glu Glu Glu Phe Ala Gln Ser Glu Glu Leu Cys Ala Lys
65                  70                  75                  80

Ala Pro Pro Pro Val Phe Tyr Asn Lys Pro Pro Glu Ile Asp Ile Thr
                85                  90                  95

Cys Trp Asp Ala Asp Pro Val Pro Glu Glu Glu Glu Gly Phe Glu Gly
            100                 105                 110

Gly Asp

<210> SEQ ID NO 3
<211> LENGTH: 649
<212> TYPE: PRT
<213> ORGANISM: Homo sapiens

<400> SEQUENCE: 3

Met Ala Gly Val Ser Phe Ser Gly His Arg Leu Glu Leu Leu Ala Ala
1               5                   10                  15

Tyr Glu Glu Val Ile Arg Glu Ser Ala Ala Asp Trp Ala Leu Tyr
            20                  25                  30

Thr Tyr Glu Asp Gly Ser Asp Asp Leu Lys Leu Ala Ala Ser Gly Glu
        35                  40                  45

Gly Gly Leu Gln Glu Leu Ser Gly His Phe Glu Asn Gln Lys Val Met
    50                  55                  60

Tyr Gly Phe Cys Ser Val Lys Asp Ser Gln Ala Ala Leu Pro Lys Tyr
65                  70                  75                  80

Val Leu Ile Asn Trp Val Gly Glu Asp Val Pro Asp Ala Arg Lys Cys
                85                  90                  95

Ala Cys Ala Ser His Val Ala Lys Val Ala Glu Phe Phe Gln Gly Val
            100                 105                 110

Asp Val Ile Val Asn Ala Ser Ser Val Glu Asp Ile Asp Ala Gly Ala
        115                 120                 125

Ile Gly Gln Arg Leu Ser Asn Gly Leu Ala Arg Leu Ser Ser Pro Val
    130                 135                 140

Leu His Arg Leu Arg Leu Arg Glu Asp Glu Asn Ala Glu Pro Val Gly
145                 150                 155                 160
```

-continued

Thr Thr Tyr Gln Lys Thr Asp Ala Ala Val Glu Met Lys Arg Ile Asn
            165                 170                 175

Arg Glu Gln Phe Trp Glu Gln Ala Lys Lys Glu Glu Leu Arg Lys
            180                 185                 190

Glu Glu Glu Arg Lys Lys Ala Leu Asp Glu Arg Leu Arg Phe Glu Gln
            195                 200                 205

Glu Arg Met Glu Gln Glu Arg Gln Gln Glu Glu Arg Glu Arg Arg
            210                 215                 220

Tyr Arg Glu Arg Glu Gln Gln Ile Glu Glu His Arg Arg Lys Gln Gln
225                 230                 235                 240

Thr Leu Glu Ala Glu Ala Lys Arg Arg Leu Lys Glu Gln Ser Ile
            245                 250                 255

Phe Gly Asp His Arg Asp Glu Glu Glu Thr His Met Lys Lys Ser
            260                 265                 270

Glu Ser Glu Val Glu Glu Ala Ala Ile Ile Ala Gln Arg Pro Asp
            275                 280                 285

Asn Pro Arg Glu Phe Phe Lys Gln Gln Glu Arg Val Ala Ser Ala Ser
            290                 295                 300

Ala Gly Ser Cys Asp Val Pro Ser Pro Phe Asn His Arg Pro Gly Ser
305                 310                 315                 320

His Leu Asp Ser His Arg Arg Met Ala Pro Thr Pro Ile Pro Thr Arg
            325                 330                 335

Ser Pro Ser Asp Ser Ser Thr Ala Ser Thr Pro Val Ala Glu Gln Ile
            340                 345                 350

Glu Arg Ala Leu Asp Glu Val Thr Ser Ser Gln Pro Pro Leu Pro
            355                 360                 365

Pro Pro Pro Pro Ala Gln Glu Thr Gln Glu Pro Ser Pro Ile Leu
            370                 375                 380

Asp Ser Glu Glu Thr Arg Ala Ala Pro Gln Ala Trp Ala Gly Pro
385                 390                 395                 400

Met Glu Glu Pro Pro Gln Ala Gln Ala Pro Arg Gly Pro Gly Ser
            405                 410                 415

Pro Ala Glu Asp Leu Met Phe Met Glu Ser Ala Glu Gln Ala Val Leu
            420                 425                 430

Ala Ala Pro Val Glu Pro Ala Thr Ala Asp Ala Thr Glu Ile His Asp
            435                 440                 445

Ala Ala Asp Thr Ile Glu Thr Asp Thr Ala Thr Ala Asp Thr Thr Val
            450                 455                 460

Ala Asn Asn Val Pro Pro Ala Ala Thr Ser Leu Ile Asp Leu Trp Pro
465                 470                 475                 480

Gly Asn Gly Glu Gly Ala Ser Thr Leu Gln Gly Glu Pro Arg Ala Pro
            485                 490                 495

Thr Pro Pro Ser Gly Thr Glu Val Thr Leu Ala Glu Val Pro Leu Leu
            500                 505                 510

Asp Glu Val Ala Pro Glu Pro Leu Leu Pro Ala Gly Glu Gly Cys Ala
            515                 520                 525

Thr Leu Leu Asn Phe Asp Glu Leu Pro Glu Pro Pro Ala Thr Phe Cys
            530                 535                 540

Asp Pro Glu Glu Val Glu Gly Glu Ser Leu Ala Ala Pro Gln Thr Pro
545                 550                 555                 560

Thr Leu Pro Ser Ala Leu Glu Glu Leu Glu Gln Glu Gln Glu Pro Glu
            565                 570                 575

```
Pro His Leu Leu Thr Asn Gly Glu Thr Thr Gln Lys Glu Gly Thr Gln
            580                 585                 590

Ala Ser Glu Gly Tyr Phe Ser Gln Ser Gln Glu Glu Phe Ala Gln
        595                 600                 605

Ser Glu Glu Leu Cys Ala Lys Ala Pro Pro Val Phe Tyr Asn Lys
    610                 615                 620

Pro Pro Glu Ile Asp Ile Thr Cys Trp Asp Ala Asp Pro Val Pro Glu
625                 630                 635                 640

Glu Glu Glu Gly Phe Glu Gly Gly Asp
                645

<210> SEQ ID NO 4
<211> LENGTH: 695
<212> TYPE: PRT
<213> ORGANISM: Homo sapiens

<400> SEQUENCE: 4

Met Ala Gly Val Ser Phe Ser Gly His Arg Leu Glu Leu Leu Ala Ala
1               5                   10                  15

Tyr Glu Glu Val Ile Arg Glu Glu Ser Ala Ala Asp Trp Ala Leu Tyr
            20                  25                  30

Thr Tyr Glu Asp Gly Ser Asp Leu Lys Leu Ala Ala Ser Gly Glu
        35                  40                  45

Gly Gly Leu Gln Glu Leu Ser Gly His Phe Glu Asn Gln Lys Val Met
    50                  55                  60

Tyr Gly Phe Cys Ser Val Lys Asp Ser Gln Ala Ala Leu Pro Lys Tyr
65                  70                  75                  80

Val Leu Ile Asn Trp Val Gly Glu Asp Val Pro Asp Ala Arg Lys Cys
                85                  90                  95

Ala Cys Ala Ser His Val Ala Lys Val Ala Glu Phe Phe Gln Gly Val
            100                 105                 110

Asp Val Ile Val Asn Ala Ser Ser Val Glu Asp Ile Asp Ala Gly Ala
        115                 120                 125

Ile Gly Gln Arg Leu Ser Asn Gly Leu Ala Arg Leu Ser Ser Pro Val
    130                 135                 140

Leu His Arg Leu Arg Leu Arg Glu Asp Glu Asn Ala Glu Pro Val Gly
145                 150                 155                 160

Thr Thr Tyr Gln Lys Thr Asp Ala Ala Val Glu Met Lys Arg Ile Asn
                165                 170                 175

Arg Glu Gln Phe Trp Glu Gln Ala Lys Lys Glu Glu Glu Leu Arg Lys
            180                 185                 190

Glu Glu Glu Arg Lys Lys Ala Leu Asp Glu Arg Leu Arg Phe Glu Gln
        195                 200                 205

Glu Arg Met Glu Gln Glu Arg Gln Glu Gln Glu Arg Glu Arg Arg
    210                 215                 220

Tyr Arg Glu Arg Glu Gln Gln Ile Glu Glu His Arg Arg Lys Gln Gln
225                 230                 235                 240

Thr Leu Glu Ala Glu Glu Ala Lys Arg Arg Leu Lys Glu Gln Ser Ile
                245                 250                 255

Phe Gly Asp His Arg Asp Glu Glu Glu Thr His Met Lys Lys Ser
            260                 265                 270

Glu Ser Glu Val Glu Glu Ala Ala Ile Ile Ala Gln Arg Pro Asp
        275                 280                 285

Asn Pro Arg Glu Phe Phe Lys Gln Gln Glu Arg Val Ala Ser Ala Ser
    290                 295                 300
```

```
Ala Gly Ser Cys Asp Val Pro Ser Pro Phe Asn His Arg Pro Gly Arg
305                 310                 315                 320

Pro Tyr Cys Pro Phe Ile Lys Ala Ser Asp Ser Gly Pro Ser Ser Ser
            325                 330                 335

Ser Ser Ser Ser Ser Ser Pro Pro Arg Thr Pro Phe Pro Tyr Ile Thr
        340                 345                 350

Cys His Arg Thr Pro Asn Leu Ser Ser Ser Leu Pro Cys Ser His Leu
            355                 360                 365

Asp Ser His Arg Arg Met Ala Pro Thr Pro Ile Pro Thr Arg Ser Pro
        370                 375                 380

Ser Asp Ser Ser Thr Ala Ser Thr Pro Val Ala Glu Gln Ile Glu Arg
385                 390                 395                 400

Ala Leu Asp Glu Val Thr Ser Ser Gln Pro Pro Leu Pro Pro Pro
            405                 410                 415

Pro Pro Pro Ala Gln Glu Thr Gln Glu Pro Ser Pro Ile Leu Asp Ser
            420                 425                 430

Glu Glu Thr Arg Ala Ala Ala Pro Gln Ala Trp Ala Gly Pro Met Glu
        435                 440                 445

Glu Pro Pro Gln Ala Gln Ala Pro Pro Arg Gly Pro Gly Ser Pro Ala
        450                 455                 460

Glu Asp Leu Met Phe Met Glu Ser Ala Glu Gln Ala Val Leu Ala Ala
465                 470                 475                 480

Pro Val Glu Pro Ala Thr Ala Asp Ala Thr Glu Ile His Asp Ala Ala
            485                 490                 495

Asp Thr Ile Glu Thr Asp Thr Ala Thr Ala Asp Thr Val Ala Asn
            500                 505                 510

Asn Val Pro Pro Ala Ala Thr Ser Leu Ile Asp Leu Trp Pro Gly Asn
            515                 520                 525

Gly Glu Gly Ala Ser Thr Leu Gln Gly Glu Pro Arg Ala Pro Thr Pro
        530                 535                 540

Pro Ser Gly Thr Glu Val Thr Leu Ala Glu Val Pro Leu Leu Asp Glu
545                 550                 555                 560

Val Ala Pro Glu Pro Leu Leu Pro Ala Gly Glu Gly Cys Ala Thr Leu
            565                 570                 575

Leu Asn Phe Asp Glu Leu Pro Gly Pro Pro Ala Thr Phe Cys Asp Pro
            580                 585                 590

Glu Glu Val Glu Gly Glu Ser Leu Ala Ala Pro Gln Thr Pro Thr Leu
        595                 600                 605

Pro Ser Ala Leu Glu Glu Leu Glu Gln Glu Gln Glu Pro Glu Pro His
            610                 615                 620

Leu Leu Thr Asn Gly Glu Thr Thr Gln Lys Glu Gly Thr Gln Ala Ser
625                 630                 635                 640

Glu Gly Tyr Phe Ser Gln Ser Gln Glu Glu Phe Ala Gln Ser Glu
            645                 650                 655

Glu Leu Cys Ala Lys Ala Pro Pro Val Phe Tyr Asn Lys Pro Pro
            660                 665                 670

Glu Ile Asp Ile Thr Cys Trp Asp Ala Asp Pro Val Pro Glu Glu Glu
            675                 680                 685

Glu Gly Phe Glu Gly Gly Asp
        690                 695
```

DETECTION OF AN AUTOANTIBODY

CROSS-REFERENCE TO RELATED APPLICATION

The present application claims the benefit to European patent application EP 19194680.5, filed Aug. 30, 2019, the content of which is hereby incorporated by reference in its entirety.

REFERENCE TO A SEQUENCE LISTING

The present application is accompanied by an ASCII text file as a computer readable form containing the sequence listing, titled "2020-07-29-Sequence-Listing," created on Jul. 29, 2020, with the file size of 14,062 bytes, which is incorporated by reference in its entirety.

BACKGROUND OF THE INVENTION

Field of the Invention

The present invention relates to a diagnostically useful carrier comprising a peptide comprising the amino acid sequence set forth in SEQ ID NO: 1, SEQ ID NO: 2, SEQ ID NO: 3, SEQ ID NO: 4 or a variant thereof, a kit, a composition, a detection method, use for detecting a neurological disease, a human autoantibody specifically binding to Drebrin and a therapeutic compound or combination for use in the treatment of a neurological use.

Description of Related Art

The notion that neuropsychiatric symptoms including recurrent seizures and impairment of cognition and behavior are linked to distinct autoantibodies has fundamentally improved the diagnostic and therapeutic approaches to several severe neurological disorders. This includes the disease spectrum of encephalitis, including limbic encephalitis (LE).

In encephalitis, the autoantibody (AB) spectrum comprises 'onconeural' ABs including amphiphysin (anti-AMPH), BMP binding endothelial regulator (anti-BMPER; anti-CV2) and paraneoplastic Ma antigen 2 (anti-Ma2; anti-PNMA2) and anti-glutamic acid decarboxylase 65 (GAD65) targeting intracellular protein structures. Autoantibodies targeting neuronal surface proteins prompt pathogenic concepts of hyperexcitability. These targets include N-methyl-D-aspartate receptors (NMDAR), voltage-gated potassium channel complex (VGKC) components such as Leucine-rich glioma inactivated 1 (LGI1) or contactin associated protein 1 (CASPR), a-amino-3-hydroxy-5-methyl-4-isoxazolepropionic acid receptors (AMPAR), c-aminobutyric acid receptor B (GABABR), dipeptidyl-peptidase-like protein-6 (DPPX), metabotropic glutamate receptor 5 (mGluR5)10 and glycine receptors (GLY-Rs).

Further examples of neurological conditions coinciding with the emergence of autoantibodies include Neuromyelitis optica, a disease characterized by loss of visual perception and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such was previously poorly understood, the risk for many of these diseases can now be assessed and treated efficiently owing to the availability of assays based on the detection of autoantibodies.

However, despite the progress in recognizing autoantibody mediated immune mechanisms in a substantial proportion of patients with encephalitis and particularly LE, in >50% of patients with suspected LE specific 'neurological' antibodies are not detected. About 70% of encephalitis cases with unclear etiology remain without definite diagnosis even after extensive evaluation for infectious etiologies. A better understanding of immunological mechanisms in so far seronegative encephalitis patients may open new therapy options for affected individuals.

SUMMARY OF THE INVENTION

Therefore, it is paramount that new approaches be developed to distinguish neurological conditions associated with autoantibodies from those that are not and assess a subject's risk of developing such a disease. Furthermore, the identification of new antigens binding to autoantibodies is required to improve diagnosis as well as therapy.

Accordingly, the present application includes the following embodiments:

1. A diagnostically useful carrier comprising a peptide comprising the amino acid sequence set forth in SEQ ID NO: 1, SEQ ID NO: 2, SEQ ID NO: 3, SEQ ID NO: 4 or a variant thereof.
2. The diagnostically useful carrier according to embodiment 1, wherein the carrier is selected from the group comprising a glass slide, a biochip, a microtiter plate, a lateral flow device, a test strip, a membrane, a line blot, a chromatography column and a bead.
3. A kit comprising the diagnostically useful carrier according to embodiment 1 or 2 and an antibody for detecting a human autoantibody.
4. A method for diagnosing a neurological disease comprising
   detecting in a sample of a patient the presence of an autoantibody specifically binding to Drebrin.
5. A composition comprising
   a) a peptide comprising the amino acid sequence set forth in SEQ ID NO: 1, SEQ ID NO: 2 or a variant thereof, and
   b) a pharmaceutically acceptable carrier.
6. A composition according to embodiment 5 or the diagnostically useful carrier according to embodiment 1 or 2 for use in the diagnosis of a neurological disease.
7. A method of detecting the presence or absence of an autoantibody specifically binding to Drebrin, comprising
   i) contacting a sample isolated from a subject having a neurological disease with a peptide comprising SEQ ID NO: 1, SEQ ID NO: 2, SEQ ID NO: 3, SEQ ID NO: 4 or a variant thereof, wherein the polypeptide binds specifically to autoantibodies binding to SEQ ID NO: 1, SEQ ID NO: 2, SEQ ID NO: 3 or SEQ ID NO: 4;
   ii) detecting the presence or absence of an autoantibody against Drebrin in a complex with the peptide.
8. Use of (i) a peptide comprising the amino acid sequence set forth in SEQ ID NO: 1, SEQ ID NO: 2, SEQ ID NO: 3, SEQ ID NO: 4 or a variant thereof or (ii) a nucleic acid vector encoding a peptide comprising the amino acid sequence set forth in SEQ ID NO: 1, SEQ ID NO: 2, SEQ ID NO: 3, SEQ ID NO: 4 or a variant thereof for the manufacture of a kit for detecting a neurological disease.
9. The method according to embodiment 4, the composition or carrier for use according to embodiment 6 or the use according to embodiment 8, wherein the neurological disease is a neurological autoimmune disease, preferably encephalitis, seizure or epilepsy.

10. The method according to embodiment 4 or 7, wherein the sample is blood, serum, plasma, cerebrospinal fluid (CSF), urine or saliva.
11. The method according to embodiment 4 or the method according to embodiment 7, wherein the autoantibody to SEQ ID NO: 1, SEQ ID NO: 2, SEQ ID NO: 3 or SEQ ID NO: 4 is selected from the group comprising IgG, IgA and IgM class antibodies.
12. The method according to embodiment 4, the method according to embodiment 7 or the use according to embodiment 8, wherein the detection comprises a blot assay, chemiluminescence immunoassay, enzyme-linked Immunosorbent assay (ELISA), light scattering immunoassay, radiolabeled immunoassay or immunofluorescence assay.
13. A human autoantibody specifically binding to Drebrin.
14. Use of a patient sample or a purified derivative of said sample each comprising an autoantibody specifically binding to Drebrin as a positive control in an immunoassay.
15. A therapeutic compound or a combination of therapeutic compounds for use in the treatment of a neurological autoimmune disease, wherein the neurological autoimmune disease is associated with autoantibodies specifically binding to Drebrin, wherein the therapeutic compound or the combination is selected from
    a) valproate, lamotrigine, levetiracetam, lacosamide, oxcarbazepine, clobazam and zonisamide; and/or
    b) an immunosuppressant and a peptide comprising the amino acid sequence set forth in SEQ ID NO: 1, SEQ ID NO: 2, SEQ ID NO: 3, SEQ ID NO: 4 or a variant thereof.
16. The therapeutic compound or the combination of therapeutic compounds for use according to embodiment 15, wherein the immunosuppressant is selected from the group consisting of prednisone, dexamethasone, hydrocortisone, azathioprine, mercaptopurine, fingolimod, myriocin, mycophenolic acid, everolimus, sirolimus, tacrolimus and ciclosporin.

BRIEF DESCRIPTION OF THE SEVERAL VIEWS OF THE DRAWINGS

FIG. 1 shows the clinico-serological parameters of anti-Drebrin AB+ patients.

FIG. 2 shows the neuropsychological dynamics in the context of clinico-serological aspects of anti-Drebrin AB+ patients.

FIG. 3A shows cMRI of patient #2, which revealed swelling and T2-hyperintensity of the right amygdaloid area (white arrow).

FIG. 3B shows cMRI of patient #2, which revealed a certain loss of the internal organoid texture of the right sided hippocampal formation (white arrow).

FIG. 3C shows that, in contrast to these circumscribed limbic changes, in patient #4 the cMRI showed extensive atrophy of the left hemisphere (white arrow) as well as some swelling of the left amygdala.

FIG. 3D shows that, in the cMRI of patient #4, there was only a slight volume reduction of the left hippocampus (white arrow).

DETAILED DESCRIPTION OF THE INVENTION

Figure 3E:
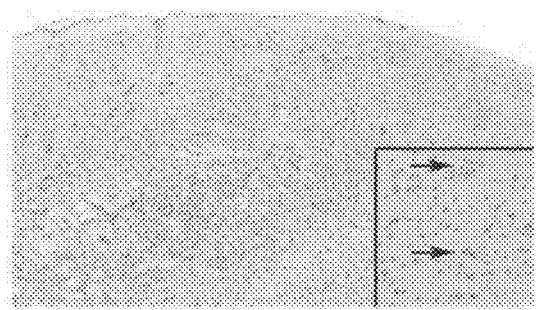
FIG. 3E shows that, on the HE (hematoxylin and eosin) staining in a cortical biopsy of patient #4, rather dense mononuclear infiltrates became visible with a focus in deeper cortical layers. There was substantial edema and besides lymphocytes clustering around neurons (E, black arrows in insert), also macrophage infiltrates were present.

The present invention relates to autoantibodies to Drebrin and assays and therapies based on their detection. As far as the inventors are aware, the existence of autoantibodies to Drebrin, let alone their usefulness, has not yet been reported in the state of the art. A number of companies have commercialized recombinant antibodies binding to Drebrin including Santa Cruz Biotechnology (C-8, sc-374269) and Abcam (M2F6, ab12350).

The problem underlying the present invention is to provide novel reagents, devices and methods that may be used to assess whether a subject is likely to develop an autoimmune disease, preferably an autoimmune disease of the nervous system, more preferably encephalitis, seizure or epilepsy.

Another problem underlying the present invention is to provide novel reagents, devices and methods that may be used to distinguish autoimmune diseases, in particular neurological autoimmune diseases, more preferably selected from the group comprising encephalitis, seizure and epilepsy, from diseases other than autoimmune diseases, for example from infections associated with neurological symptoms, not in the least to determine the most promising treatment regimen, more specifically whether or not an immunosuppressive treatment is adequate, preferably well before the onset of the disease.

The problem underlying the present invention is solved by the subject-matter of the attached independent and dependent claims.

In a first aspect, the problem is solved by a diagnostically useful carrier comprising a peptide comprising the amino acid sequence set forth in SEQ ID NO: 1, SEQ ID NO: 2, SEQ ID NO: 3, SEQ ID NO: 4, or a variant thereof.

In a second aspect, the problem is solved by a kit comprising the diagnostically useful carrier of the invention and an antibody for detecting a human autoantibody.

In a third aspect, the problem is solved by a method for diagnosing a neurological disease comprising detecting in a sample of a patient the presence of an autoantibody specifically binding to Drebrin.

In a $4^{th}$ aspect, the problem is solved by a composition comprising a) a peptide comprising the amino acid sequence set forth in SEQ ID NO: 1, SEQ ID NO: 2 or a variant thereof, and b) pharmaceutically acceptable carrier.

In a $5^{th}$ aspect, the problem is solved by a composition of the invention or the diagnostically useful carrier of the invention for use in the diagnosis of a neurological disease.

In a $6^{th}$ aspect, the problem is solved by a method of detecting the presence or absence of an autoantibody specifically binding to Drebrin, comprising i) contacting a sample isolated from a subject having a neurological disease with a peptide comprising SEQ ID NO: 1, SEQ ID NO: 2, SEQ ID NO: 3, SEQ ID NO: 4, or a variant thereof, wherein the polypeptide binds specifically to autoantibodies binding to SEQ ID NO: 1, SEQ ID NO: 2, SEQ ID NO: 3, or SEQ ID NO: 4; ii) detecting the presence or absence of an autoantibody against Drebrin in a complex with the peptide.

In a $7^{th}$ aspect, the problem is solved by use of (i) a peptide comprising the amino acid sequence set forth in SEQ ID NO: 1, SEQ ID NO: 2, SEQ ID NO: 3, SEQ ID NO: 4, or a variant thereof or (ii) a nucleic acid vector encoding a peptide comprising the amino acid sequence set forth in SEQ ID NO: 1, SEQ ID NO: 2, SEQ ID NO: 3, SEQ ID NO: 4, or a variant thereof for the manufacture of a kit for detecting a neurological disease.

In an $8^{th}$ aspect, the problem is solved by a human autoantibody specifically binding to Drebrin.

In a $9^{th}$ aspect, the problem is solved by a therapeutic compound or a combination of therapeutic compounds for use in the treatment of a neurological autoimmune disease, wherein the neurological autoimmune disease is associated with autoantibodies specifically binding to Drebrin, wherein the therapeutic compound or the combination is selected from a) valproate, lamotrigine, levetiracetam, lacosamide, oxcarbazepine, clobazam and zonisamide; and/or b) an immunosuppressant and a peptide comprising the amino acid sequence set forth in SEQ ID NO: 1, SEQ ID NO: 2, SEQ ID NO: 3, SEQ ID NO: 4, or a variant thereof.

In a $10^{th}$ aspect, the problem is solved by the use of a patient sample or a purified derivative of said sample each comprising an autoantibody specifically binding to Drebrin as a positive control in an immunoassay.

In a preferred embodiment, the immunoassay is a diagnostic immunoassay comprising the examination of a fluid for which the presence or absence of an autoantibody specifically binding to Drebrin is not known.

In a preferred embodiment, the carrier is selected from the group comprising a glass slide, a biochip, a microtiter plate, a lateral flow device, a test strip, a membrane, a line blot, a chromatography column and a bead.

In a preferred embodiment, the neurological disease is a neurological autoimmune disease, preferably encephalitis, seizure or epilepsy.

In a preferred embodiment, the sample is blood, serum, plasma, cerebrospinal fluid (CSF), urine or saliva.

In a preferred embodiment, the autoantibody to SEQ ID NO: 1, SEQ ID NO: 2, SEQ ID NO: 3, or SEQ ID NO: 4 is selected from the group comprising IgG, IgA and IgM class antibodies.

In a preferred embodiment, the detection comprises a blot assay, chemiluminescence immunoassay, enzyme-linked Immunosorbent assay (ELISA), light scattering immunoassay, radiolabeled immunoassay or immunofluorescence assay.

In a preferred embodiment, the immunosuppressant is selected from the group consisting of prednisone, dexamethasone, hydrocortisone, azathioprine, mercaptopurine, fingolimod, myriocin, mycophenolic acid, everolimus, sirolimus, tacrolimus and ciclosporin.

The present invention is based on the inventors' surprising finding that an autoantibody to Drebrin exists and that the appearance of this autoantibody correlates with several neurological conditions found in patients, especially encephalitis, seizure and epilepsy. Therefore, the detection of said autoantibody can be used as a diagnostic biomarker assay. In addition, the inventors were also allowable to identify two specific regions of Drebrin that demonstrate binding activity towards these autoantibodies. Moreover, reducing the amount of the anti-Drebrin autoantibody with immunosuppressant drugs significantly improves the conditions of the patients. Thus, the anti-Drebrin autoantibody can be used a therapeutic target.

Without wishing to be bound to any theory, the presence of such autoantibodies suggests that the function of Drebrin and/or downstream effectors will be impaired in patients having such anti-Drebrin autoantibodies to the effect that neurological symptoms occur.

Drebrin (UniProt Q16643 [human] and Q9QXS6 [mouse]) is a protein encoded by the DBN1 gene. The protein is a cytoplasmic actin-binding protein playing a role in the process of neuronal growth. Drebrin is a member of the drebrin family of proteins whose regulation correlates with development of the brain. A decrease in the amount of Drebrin in the brain has been implicated as a possible contributing factor in the pathogenesis of memory disturbance in Alzheimer's disease. At least two alternative splice variants encoding different protein isoforms, such as Drebrin E (SEQ ID NO: 3) and Drebrin A (SEQ ID NO: 4) have been described. Sequence of human, mouse and rat Drebrin, which are preferred targets of the autoantibodies of the invention as well as preferred means for use and methods of the invention, are well known in the art.

The present invention relates to a polypeptide comprising a mammalian, preferably human polypeptide of Drebrin or antigenic variants reactive to autoantibodies binding to Drebrin. Mammalian Drebrin includes homologues from human, monkey, mouse, rat, rabbit, guinea pig or pig, preferably human.

In a more preferred embodiment, Drebrin is the polypeptide encoded by SEQ ID NO: 3 or SEQ ID NO: 4 (UniProtKB reference: Q16643 and Q16643-3; NM_004395, NM_080881, NM_001363541, NM_001364151, NM_001364152). Throughout this application, any data base codes cited refers to the Uniprot data base, more specifically the version on the filing date of this application or its earliest priority application.

The teachings of the present invention may not only be carried out using polypeptides, in particular a polypeptide comprising the native sequence of a polypeptide such as Drebrin or nucleic acids having the exact sequences referred to in this application explicitly, for example by function, name, sequence or accession number, or implicitly, but also using variants of such polypeptides or nucleic acids.

In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100, 200, 300, 400, 500, 750, 1000 or more amino acids. In preferred alternative embodiments, the variant has a length of not more than 645, not more than 640, not more than 630, not more than 620, not more than 610, not more than 600, not more than 550, not more than 500, not more than 450, not more than 400, not more than 350, not more than 300, not more than 250, not more than 200, not more than 180 or not more than 160 amino acids. In more preferred embodiments, the variants, particularly the above mentioned length restricted variants, comprise the amino acid sequence set forth in SEQ ID Nos. 3 and/or 4. Aside the sequence of SEQ ID Nos. 3 and/or 4 the length restricted polypeptides may further comprise sequence fragments originating from Drebrin and/or non-Drebrin fragments, such as tags.

In other preferred embodiments, the variant has at least 80%, at least 85%, at least 90%, at least 95%, at least 97% or at least 99% sequence identity to SEQ ID NO: 3 and comprises the complete of SEQ ID NO: 1 and/or SEQ ID NO: 2.

The term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In preferred embodiments, the variants and/or fragments comprise or encode for a sequence set forth in SEQ ID NO: 1 and/or SEQ ID NO: 2.

In a preferred embodiment, the variant is a linear, non-folded polypeptide, which is optionally denatured.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant. In more preferred embodiments, the serine at position 647 of SEQ ID NO: 4 is phosphorylated.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in general is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment, such biological activity is the ability to bind specifically to an autoantibody binding to Drebrin, as found in a patient suffering from an autoimmune disease associated with such autoantibody, preferably associated with a neurological disease or condition such encephalitis, seizure or epilepsy. For example, whether or not a variant of Drebrin has such biological activity may be checked by determining whether or not the variant of interest binds to an autoantibody from a sample of a patient which autoantibody binds to wild type Drebrin, preferably as determined by indirect immunofluorescence, enzyme-linked immunosorbent assay (ELISA), chemiluminescence immunoassay (CLIA) or line blot assay as for example described in the experimental section of this application.

In preferred embodiments, the variant of Drebrin is a mammalian Drebrin lacking at least 310, at least 300, at least 250, at least 200, at least 150, at least 100, at least 70, at least 50, at least 30, at least 20, at least 10, at least 5, at least at least 10, at least 5, at least 4, at least 3, at least 2 or one amino acid of the N-terminus of the corresponding naturally occurring wildtype protein. In more preferred embodiments, the variant of Drebrin is amino acids 319 to 444 and/or amino acids 536 to 649 of human Drebrin E according to SEQ ID NO: 3 or a corresponding sequence of any other mammalian species determined by sequence alignment.

Any polypeptide according to the present invention, when used to carry out the teachings of the present invention, may be provided in any form and at any degree of purification, from liquid samples, tissues or cells comprising said polypeptide in an endogenous form, more preferably cells over-expressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the inventive polypeptide is provided in the form of tissue, it is preferred that the tissue is mammalian tissue, for example human, rat, primate, donkey, mouse, goat, horse, sheep, pig or cow, more preferably brain tissue, most preferably dendrite comprising brain tissue such as cerebellum and hippocampus. If a cell lysate is used, it is preferred that the cell lysate comprises the cytoplasmic fraction. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow.

The polypeptide used to carry out the inventive teachings, including any variants, is preferably designed such that it comprises at least one epitope recognized by and/or binds specifically to the autoantibody binding to Drebrin. Said epitope may demonstrate strongest binding to autoantibody binding to native Drebrin compared with the binding observed towards other (auto)antibodies. In one embodiment, such polypeptide comprises a stretch of 6, 7, 8, 9, 10, 11, 12, 20, 25, 30, 40, 50, 60, 70, 80, 90, 100, 113, 125 or more, preferably at least 9 but no more than 16, consecutive amino acids from Drebrin. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogenes, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

The inventive polypeptide, when used according to the present invention, may be provided in any kind of conformation. For example, the polypeptide may be an essentially unfolded, a partially or a fully folded polypeptide. In a preferred embodiment, the polypeptide is folded in the sense that the epitopes essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

The inventive polypeptide may be a fusion protein which comprises amino acid sequences other than those taken from Drebrin, in particular a C-terminal or N-terminal tag, preferably a N-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilization techniques for microfluidic assays, Biomicrofluidics 7(4), 041501. In addition, various reagents and kits for immobilization reactions are commercially available, for example from Pierce Biotechnology.

It is essential that the solution or sample used for the detection of autoantibodies according to the present invention comprises antibodies, also referred to as immunoglobulins. Typically the sample of a bodily fluid comprises a representative set of the entirety of the subject's immunoglobulins. However, the sample or solution, once provided, may be subjected to further processing which may include fractionation, centrifugation, enriching or isolating the entirety of immunoglobulins or any immunoglobulin class of the subject, which may affect the relative distribution of immunoglobulins of the various classes.

The reagents, devices, methods and uses described throughout this application may be used for the identifying a subject who has an increased risk of suffering from a disease. In a preferred embodiment, the disease is a neurological disease. In a more preferred embodiment, the term "neurological disease", as used herein, refers to any disease associated with a defect of the nervous system. In another preferred embodiment, the disease is an autoimmune (or autoantibody) related neurological disease. This means that the neurological conditions are directly or indirectly caused by autoantibodies binding to native Drebrin. Thus, in a preferred embodiment, any method or use according to the present invention may be for identifying a subject having a neurological disease, preferably an autoimmune related neurological disease and even more preferably an autoimmune related neurological disease associated with autoantibodies specifically binding to Drebrin. In further more preferred embodiments, the disease is encephalitis, seizure and/or epilepsy. In other preferred embodiments, the encephalitis is a limbic encephalitis (LE). Moreover, in alternative preferred embodiments of the invention, the disease is bradycardia, increased cerebrospinal fluid (CSF) protein content, swelling of the amygdala and hippocampi or hippocampal sclerosis. In addition, the patient suffering from the neurological disease may additionally suffer from cancer, preferably from leukemia such as chronic granulocytic leukemia (CGL).

In many cases the mere detection, in other words determining whether or not detectable levels of the antibody are present, is sufficient for the assessment. If the autoantibody can be detected, this will be information instrumental for the clinician and indicates an increased likelihood that the patient will suffer from a disease. In a preferred embodiment, the autoantibody is deemed detectable if it can be detected using one or more methods selected from the group comprising immunoprecipitation, indirect immunofluorescence, ELISA, CLIA or line blot, preferably indirect immunofluorescence. In preferred embodiments, the detection of the autoantibody is carried out using a quantitative or qualitative detection. In alternative preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 2, preferably 5, 10, 20, 25, 50, 100, 200, 500, 1000, 10000 or 100000 times higher than the concentration found in the average healthy subject. In a preferred embodiment, the relative concentration of the autoantibody is determined using one or more methods selected from the group comprising semi-quantitative immunoprecipitation, semi-quantitative indirect immunofluorescence, ELISA, CLIA or semi-quantitative line blot, preferably ELISA or CLIA. Experimental details are as described in the experimental section of this application or as in textbooks or practical manuals as available at the priority date of this application.

The person skilled in the art will appreciate that a clinician does usually not conclude whether patient subject will be likely to suffer from a disease, condition or disorders solely on the basis of a single parameter, but needs to take into account other aspects, for example the presence of other autoantibodies, markers, blood parameters, clinical assessment of any symptoms or the results of medical imaging or other non-invasive methods such as polysomnography. See Baenkler H. W. (2012), General aspects of autoimmune diagnostics, in Renz, H., Autoimmune diagnostics, 2012, de Gruyter, page 3. The value of the agent or method according to the present invention may also reside the possibility to rule out the development of one disease. In a preferred embodiment, the meaning of any symptoms or diseases referred to throughout this application is in line with the person skilled in the art's understanding as of the filing date or, preferably, earliest priority date of this application as evidenced by textbooks and scientific publications.

The inventive method, polypeptide or use, optionally for determining whether a is likely to develop a disease, may comprise obtaining a sample or solution comprising antibodies, preferably from a human subject, determining whether an autoantibody binding to Drebrin is present, wherein said determining is performed by contacting the sample with the inventive polypeptide and detecting whether binding occurs between said polypeptide and said autoantibody, preferably using a labeled secondary antibody, wherein said autoantibody binds to said polypeptide if present in the sample, and assessing the patient as being more likely to suffer from said disease if the autoantibody was determined to be present in the sample or solution.

The present invention relates to a complex comprising an antibody, preferably autoantibody, binding to the inventive polypeptide. Such a complex may be used or detected as part of a method for identifying a subject who has an increased risk of developing a disease. A liquid sample comprising antibodies from a subject may be used to practice the method if an autoantibody to Drebrin is to be detected. Such a liquid sample may be any bodily fluid comprising a representative set of antibodies from the subject, preferably a sample comprising antibodies of an immunoglobulin class from the subject selected from the group comprising IgG, IgA and IgM class antibodies, preferably IgG, more preferably IgG1 and IgG2, more preferably IgG1. For example, a sample may be cerebrospinal fluid (CSF), blood or blood serum, lymph, interstitial fluid and is preferably serum or CSF, more preferably CSF. It is preferably an ex vivo sample.

The step contacting a liquid sample or solution comprising antibodies with the inventive polypeptide(s) may be carried out by incubating an immobilized form of said polypeptide(s) in the presence of the sample or solution comprising antibodies under conditions that are compatible with the formation of the complex comprising the respective polypeptide and an antibody, preferably an autoantibody, binding to the inventive polypeptide. The liquid sample or solution, then depleted of antibodies binding to the inventive polypeptide(s) may be removed subsequently, followed by one or more washing steps. Finally the complex comprising the antibody or antibodies and the polypeptide(s) may be detected. In a preferred embodiment, the term "conditions compatible with the formation of the complex" are conditions that allow for the specific antigen-antibody interactions to build up the complex comprising the polypeptide and the antibody. In a preferred embodiment such conditions may comprise incubating the polypeptide in sample diluted 1:100 in PBS buffer for 30 minutes at 25° C. In a preferred embodiment, the term "autoantibody", as used herein, refers to an antibody binding specifically to an endogenous molecule of the animal, preferably mammal, which produces said autoantibody, wherein the level of such antibody is more preferably elevated compared the average of any other antibodies binding specifically to such an endogenous molecule. In a more preferred embodiment, the autoantibody is an autoantibody binding to Drebrin, in even more preferred embodiments the autoantibody is a human autoantibody binding to Drebrin.

The method according to the present invention is preferably an in vitro method. In even more preferred embodiments, the composition of the invention and/or the diagnostically useful carrier of the invention are used in the in vitro diagnosis of a neurological disease.

In a preferred embodiment, the detection of the complex for the prognosis, assessment, identification, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, preferably ELISA, chemiluminescence immunoassays, and immunofluorescence, preferably indirect immune-fluorescence techniques. The person skilled in the art is familiar with these methods, which are also described in the state of the art, for example in Zane, H. D. (2001), Immunology—Theoretical & Practical Concepts in Laboratory Medicine, W. B. Saunders Company, in Chapter 14.

Alternatively, a sample comprising tissue comprising the inventive polypeptide rather than a liquid sample may be used. The tissue sample is preferably from a tissue expressing endogenous Drebrin, preferably at an increased level compared to the average tissue in the respective organism's, preferably human body. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed is likely to suffer in the future from a disease. If a patient is being treated and the method for obtaining diagnostically relevant information is performed again, the amount of complex detected in both runs may be correlated to find out about the progression of the disease and/or the success of a treatment.

In a preferred embodiment, the present invention provides an apparatus for analyzing a sample from a patient to detect one or more antibodies indicating an increased likelihood of a neurological autoimmune disease, wherein the antibody is an autoantibody specifically binding to Drebrin, comprising:
a. a carrier, which contains a means for capturing at least one antibody from the sample when the sample is contacted with the carrier;
b. a detectable means capable of binding to the antibody captured by the carrier when the detectable means is contacted with the carrier, particularly the detectable means is a labeled secondary antibody capable of binding to the antibody captured on the carrier;
c. optionally a means for removing any sample from the carrier and the detectable means, preferably by washing;
d. a detecting device for detecting the presence of the detectable means and converting the results into an electrical signal; and
e. optionally a means for receiving the electronical signal from the detecting device and determining if the level of the signal is indicative of an increased likelihood of a neurological autoimmune disease, in particular an increased likelihood of an encephalitis, seizure or epilepsy, by comparing with the level of signal detected in the background or an input reference value obtained with samples from healthy subjects.

In another preferred embodiment, the prognosis, assessment, identification, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immunofluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Lübeck, Germany.

A sample may be subjected to a test to determine only whether an autoantibody binding to Drebrin is present, but it is preferred that methods, tests, devices and the like contemplate determining the presence of autoantibodies to one or more additional polypeptides, preferably related to neurological autoimmune diseases, preferably selected from, more preferably all from the group comprising Hu, Yo, Ri, CV2, PNMA1, PNMA2, DNER/Tr, ARHGAP26, ITPR1, ATP1A3, NBC1, Neurochondrin, CARPVIII, Zic4, Sox1, Ma, MAG, MPO, MBP, GAD65, amphiphysin, recoverin, GABA A receptor (EP13189172.3), GABA B receptor (EP2483417), glycine receptor, gephyrin, IgLON5 (US2016/0349275), DPPX (US2015/0247847), aquaporin-4, MOG, NMDA receptor, AMPA receptors, GRM1, GRM5, LGI, VGCC und mGluR1 and CASPR2, which antigens are preferably immobilized, for example on a medical device such as a line blot. The relevant markers Neurochondrin (EP15001186), ITPR1 (EP14003703.7), NBC1 (EP14003958.7), ATP1A3, also referred to as alpha 3 subunit of human neuronal Na(+)/K(+) ATPase (EP14171561.5), Flotillin1/2 (EP3101424), NSF, STX1B and VAMP2 (EP17001205.8) and RGS8 (EP17000666.2), which have been described in the state of the art.

According to the teachings of the present invention, an antibody, preferably an autoantibody binding to the inventive polypeptide used for the assessment or identification is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the autoimmune and/or neurological disorder identified by the inventors may be used as the source.

According to the invention, an antibody, for example a human autoantibody, is provided that is capable of binding specifically to Drebrin. Vice versa, a variant of Drebrin binds specifically to an autoantibody binding specifically to Drebrin. In a preferred embodiment, the term "antibody", as used herein, refers to any immunoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "specific binding", "binding specifically" or "specifically capturing", as interchangeably used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7. The antibody may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. The antibody may be glycosylated or non-glycosylated. The person skilled in the art is familiar with methods that may be used for the identification, production and purification of antibodies and variants thereof, for examples those described in EP 2 423 226 A2 and references therein.

The present invention provides a method for isolating an autoantibody binding to Drebrin, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Suitable methods are described in the state of the art, for example in the Handbooks "Affinity chromatography", "Strategies for Protein Purification" and "Antibody Purification" (2009/2010), published by GE Healthcare Life Sciences, and in in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, intrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject. In a preferred embodiment, the invention provides a vaccine comprising the inventive polypeptide, optionally comprising an auxiliary agent such as an adjuvant or a buffer, and the use of the inventive polypeptide for the preparation of a vaccine.

As used herein, "pharmaceutically acceptable carrier" includes any and all solvents (e.g. water and water-based buffers), dispersion media, coatings, antibacterial and antifungal agents, isotonic and absorption delaying agents, and the like that are physiologically compatible. Preferably, the carrier is suitable for topical, oral, buccal, vaginal, rectal, pulmonary, nasal, transdermal, intravenous, intramuscular, subcutaneous, intrathecal, intracerebral, or parenteral administration (e.g., by injection). Excipients include pharmaceutically acceptable stabilizers and disintegrants. The use of such media and agents for pharmaceutically active substances is well known in the art. Except insofar as any conventional media or agent is incompatible with the peptidic compound, use thereof in the pharmaceutical formulations is contemplated. Supplementary active compounds can also be incorporated into the compositions.

Within the scope of the present invention, a medical device comprising, preferably coated with a reagent for detecting the inventive (auto)antibody and/or the inventive polypeptide is provided. Preferably such a medical device comprises the inventive polypeptide in a form that allows contacting it with an aqueous solution, more preferably the liquid human sample, in a straightforward manner. In particular, the inventive polypeptide comprising may be immobilized (directly or indirectly) on the surface of a carrier, preferably selected from the group comprising glass plates or slides, biochips, microtiter plates, beads, for example magnetic beads, apheresis devices, chromatography columns, membranes or the like. Exemplary medical devices include line blots, microtiter plates, glass slides for microscopy, beads, preferably magnetic beads, and biochips. In addition to the inventive polypeptide, the medical or diagnostic device may comprise additional polypeptides, for example positive or negative controls such as samples comprising or not comprising an antibody binding to the polypeptide of interest, or known other antigens binding to autoantibodies of diagnostic value, particularly those related other diseases associated with one or more identical or similar symptoms.

The inventive teachings provide a kit, preferably for identifying a subject having an increased risk for developing a disease. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the polypeptide according to the present invention and a negative control, for example a protein having no detectable affinity to the inventive polypeptide such as bovine serum albumin. Finally, such a kit may comprise a standard solution of an antibody binding to Drebrin for preparing a calibration curve.

In a preferred embodiment, the kit comprises a means for detecting an autoantibody binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. More preferably said labeled secondary antibody specifically binds to human IgG, IgA or IgM. A multitude of methods and means for detecting such a complex have been described in the state of the art, for example in Philips, Terry, M., Analytical techniques in immunochemistry, 1992, Marcel Dekker, Inc.

As used herein, "label", "detectable label", or "marker", or "detectable marker", which are interchangeably used in the specification, refers to any chemical moiety attached to a protein or nucleic acid, wherein the attachment may be covalent or non-covalent. Preferably, the label is detectable and renders the protein or nucleic acid detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

Drebrin or a variant thereof may be produced or provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid. The person skilled in the art is familiar with a variety of suitable vectors, of which are commercially available, for example from Origene. For example, a vector encoding for fusion constructs with a N-terminal GFP may be used. The cell may be a eukaryotic or prokaryotic cell, preferably of eukaryotic cell, such as a yeast cell, and is more preferably a mammalian, more preferably a human cell such as a HEK293 cell. Examples of a mammalian cell include a HEK293, CHO or COS-7 cell. The cell comprising the nucleic acid encoding for the inventive polypeptide may be a recombinant cell or an isolated cell wherein the term "isolated" means that the cell is enriched such that, compared to the environment of the wild type of said cell, fewer cells of other differentiation or species or in fact no such other cells are present.

In a preferred embodiment, the medical device according to the present invention, preferably a slide suitable for microscopy, comprises one or more, preferably all components from the group comprising a first eukaryotic cell expressing, preferably overexpressing Drebrin or a variant thereof, a eukaryotic, preferably mammalian tissue expressing endogenous Drebrin such as rat or primate cerebellum, a second eukaryotic cell, which is the same type of cell as the first eukaryotic cell, but does not express or overexpress Drebrin. The first and the second eukaryotic cell are cultured cells derived from an isolated cell line such as HEK293. Preferably, the first and the second cell are each transfected with a vector sharing the same backbone, wherein the vector used to transfect the first cell comprises a nucleic acid encoding Drebrin or a variant thereof and the vector used to transfect the second cell does not comprise Drebrin or a variant thereof. The second cell may serve as a negative control. The components (cells and tissue) may be spatially separate on the medical device, such that they may be evaluated independently, with no antigen from one reagent contaminating another. In a more preferred embodiment, the first and/or the second cell is a fixed cell, for example fixed using methanol or acetone. Protocols for fixing cells are described in the state of the art. As an additional component, a secondary labeled antibody, preferably labeled with a fluorescent dye may be provided. The components and the medical device may be part of a kit.

In a preferred embodiment, a microtiter plate, membrane, blot such as dot blot or line blot is used to carry out the diagnostic method according to the invention. The person skilled in the art is familiar with the experimental setup of a line blot, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). If the medical device is a line blot, it may comprise Drebrin or a variant thereof immobilized on a membrane, preferably in the shape of a test stripe. The membrane may comprise one or more additional antigens, spatially separated from Drebrin. The membrane may comprise a control band indicating addition of the sample such as a blood sample and/or a control band indicating addition of a secondary antibody. A kit may comprise any component, preferably all from the group comprising the line blot, a secondary antibody and a washing solution.

In another preferred embodiment, the medical device is a microtiter plate comprising at least 8 wells. At least one of the wells is directly or indirectly coated with Drebrin or a variant thereof. At least 3, preferably 4, more preferably 5 calibrators are provided that comprise an antibody to Drebrin at a defined concentration and may be used to set up a calibration curve for semi-quantitative analysis. A secondary antibody comprising an enzymatically active label may be provided. A kit may comprise any component, preferably all from the group comprising the microtiter plate, the calibrators, a washing solution and the secondary antibody.

In another preferred embodiment, the medical device is a bead coated directly or indirectly with Drebrin or a variant thereof. The bead may be selected from the group comprising a magnetic bead and a fluorescent bead. A secondary antibody comprising a label capable of providing chemiluminescence or fluorescence may be used. A positive control comprising an antibody to Drebrin may be provided. At least 3, preferably 4, more preferably 5 calibrators may be provided that comprise an antibody to Drebrin at a defined concentration and may be used to set up a calibration curve for semi-quantitative analysis. If the label is capable of generating chemiluminescence, a solution may be provided that comprises additional components required for the chemiluminescence reaction. For example, if the label is an enzyme, the solution comprises substrates. If the label is a compound capable of generating chemiluminescence such as an acridinium ester, additional compounds required for the reaction are provided in the solution. A kit may comprise any component, preferably all from the group comprising the bead, the secondary antibody, the calibrators, a washing solution and the solution comprising additional components.

The inventive teachings may not only be used for an assessment or identification, but also for preventing or treating a disease, more specifically a method for preventing or treating a disease, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolatemofetil, intravenous immunoglobulin, tacrolimus, cyclosporine, methotrexate, azathioprine, dexamethasone, hydrocortisone, mercaptopurine, fingolimod, myriocin, mycophenolic acid, everolimus, sirolimus, valproate, lamotrigine, levetiracetam, lacosamide, oxcarbazepine, clobazam, zonisamide and/or the pharmaceutical composition.

In a preferred embodiment, the present invention provides a use of a reagent for the detection of an autoantibody to Drebrin or a reagent binding to such autoantibody, or of a nucleic acid encoding Drebrin or the variant or a nucleic acid hybridizing specifically to a nucleic acid encoding Drebrin or a vector or cell comprising said nucleic acid for the manufacture of kit for the diagnosis of a disease.

In a preferred embodiment, any method or use according to the present invention may be intended for testing in vitro the efficiency of a medical device designed to remove an autoantibody from a patient's blood, wherein the testing is performed on a liquid other than patient's blood. After the use of the medical device with a patient, its capacity to remove autoantibody may be checked by running a solution comprising antibody to Drebrin through the device, followed by use of the method according to the present invention to confirm that less or no antibody is in the solution that has been passed through the device, i.e. showing that the device has still the capacity to remove antibody from the solution. Alternatively, from a batch comprising a large number of devices, a small number of devices may be tested for confirming or testing the quality of the entire batch in the sense of quality control, wherein the sample or solution may comprise a known concentration of antibody to Drebrin.

In another preferred embodiment, the method may be for confirming the reliability of an antibody detection assay and may involve detecting an antibody to Drebrin in a solution, which is not a sample from a patient, but is known to comprise an antibody to Drebrin, preferably at a known concentration. Alternatively, the solution may be a negative control not comprising the antibody to check the background. Such method may be run in parallel with, after or before a diagnostic method. In a preferred embodiment, any method or use according to the present invention may be intended for generating an autoantibody profile, preferably for detecting a disease in a mammal, preferably a human. In a preferred embodiment, any method or use may be for detecting disease-associated markers in a sample from neurological disease patients.

In a preferred embodiment, any method or use according to the present invention may be for identifying a subject at risk of suffering from or developing a neurological disease, preferably an autoimmune related neurological disease.

FIG. 1 shows the clinico-serological parameters of anti-Drebrin AB$^+$ patients. Legend: Pat.—Patient; age—age of seizure onset; m—male; f—female; ANA—antinuclear antibodies; neg.—negative; CSF—cerebrospinal fluid; ↑—increase; ↓—decrease; pleoc.—pleocytosis; EEG—Electroencephalography; L—left; R—right; bilat—bilateral; temp—temporal; front—frontal; CGL—chronic granulocytic leukemia; FD—first diagnosis; MTX—methotrexate; Pred.—prednisolone; MRI—magnet resonance imaging; hip—hippocampus; amy—amygdala; hem—hemisphere; swelling—volume increase and T2/FLAIR-hyperintensity; V—volume.

FIG. 2 shows the neuropsychological dynamics in the context of clinico-serological aspects of anti-Drebrin AB$^+$ patients. Legend: Pat.—Patient; AED—antiepileptic drug, numbers refer to daily dosage in mg; Val—Valproate; Lam—lamotrigine; Lev—levetiracetam; Lac—lacosamide; Oxc—oxcarbazepine; Clob—clobazam; Zon—zonisamid; IS—immunosuppressant therapy; Pred. (p.)—prednisolone (pulse); MRI—magnet resonance imaging; R—right; L—left; ↑—volume increase; ↓—volume decrease; hip—hippocampus; amy—amygdala; hemis—hemisphere; par—parietal; temp-pol—temporopolar; AB status—anti-Drebrin autoantibody status, numbers refer to specific titers; s—serum; c sf—cerebrospinal fluid; Exec./Verb./Fig. Mem.—executive/verbal/figural memory; BDI—Becks Depression Inventory; empty space: no data available for these timepoints; for IQ, Exec./Verb./Fig. Mem., BDI: ++++—performance above average; +++—average performance; ++—performance 1SD below average; +—performance 2SD below average; 0—performance >2SD below average; 1(06/13).

Figure 3F:
FIG. 3F shows that the mononuclear infiltrates corresponded to CD3 positive T-lymphocytes (black arrow).
Figure 3G:
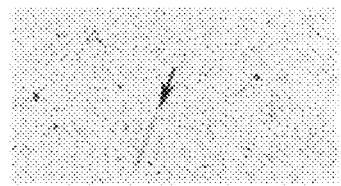
FIG. 3G shows CD8 positive T-lymphocytes clustered around blood vessel structures (arrow) and in intraparenchymal localization.
Figure 3H:
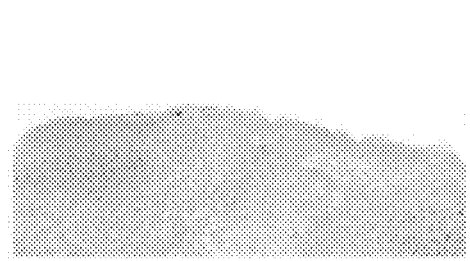
FIG. 3H shows immunohistochemistry with antibodies against NeuN (neuronal nuclei) demonstrated substantial neuronal cell loss in the lower cortical layers.
Figure 3I:
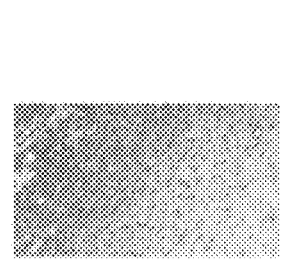
FIG. 3I shows that, concomitantly, extensive fibrillary and cellular astrogliosis was present in the GFAP immunohistochemistry.
Figure 3J:
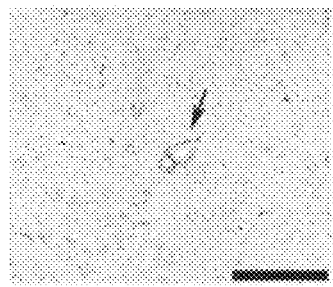
FIG. 3J shows that, correspondingly, immunohistochemistry with antibodies against HLA-DR demonstrated extensive activated, highly ramified microglial infiltrates as well as the presence of macrophages, some of them in perivascular localization (black arrow; bar graph corresponds to 200 μm in E, G & H, 50 μm in insert in E, 100 μm in F, I and J). No syndecan positive plasma cells were present (data not shown).
Figure 4A:
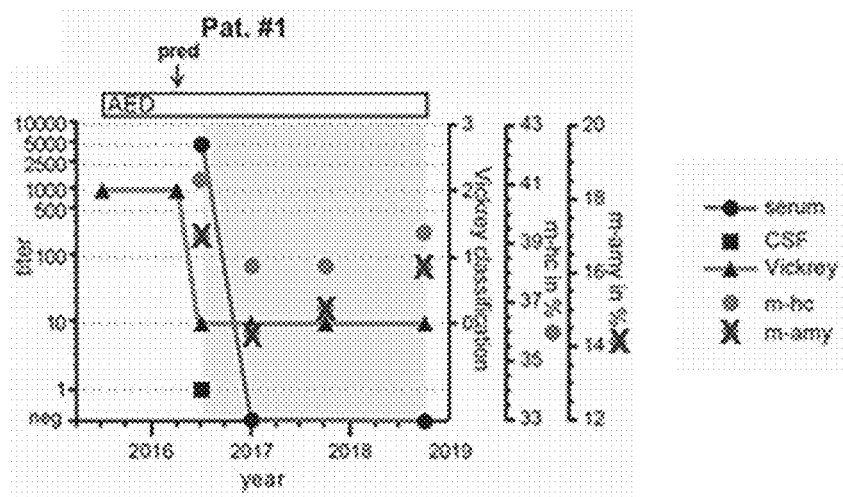
FIG. 4A shows dynamics of seizures and anti-Drebrin autoantibody titers correlated to therapeutic aspects for Patient #1. Seizure free intervals are highlighted in grey. Outcome (triangle) is reported based on Vickrey's classification: 0—seizure free, 1—aura, 2—1-10 seizures/year; 3—>10 seizures/year. Amygdala/hippocampal volume (isometric T1-sequence) is given as mean relative volume of both amygdalae/hippocampi (mamy/m-hc) in percent. AED—anti-epileptic drugs; pred—prednisolone pulse.
Figure 4B:
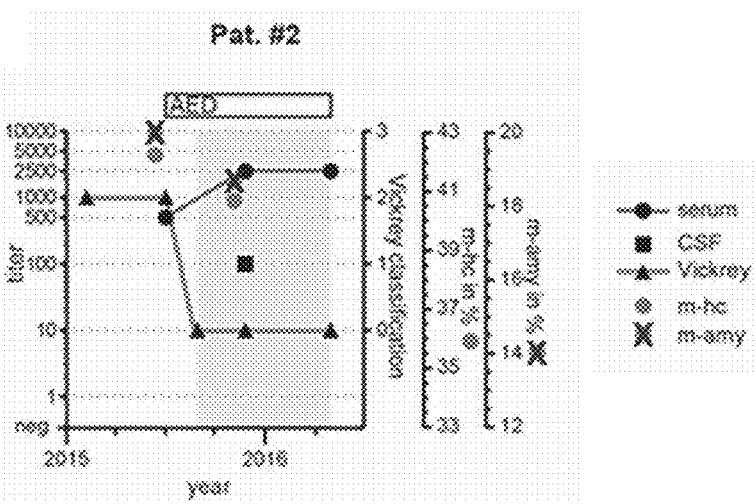
FIG. 4B shows dynamics of seizures and anti-Drebrin autoantibody titers correlated to therapeutic aspects for Patient #2. Seizure free intervals are highlighted in grey. Outcome (triangle) is reported based on Vickrey's classification: 0—seizure free, 1—aura, 2—1-10 seizures/year; 3—>10 seizures/year. Amygdala/hippocampal volume (isometric T1-sequence) is given as mean relative volume of both amygdalae/hippocampi (mamy/m-hc) in percent. AED—anti-epileptic drugs; pred—prednisolone pulse.
Figure 4C:
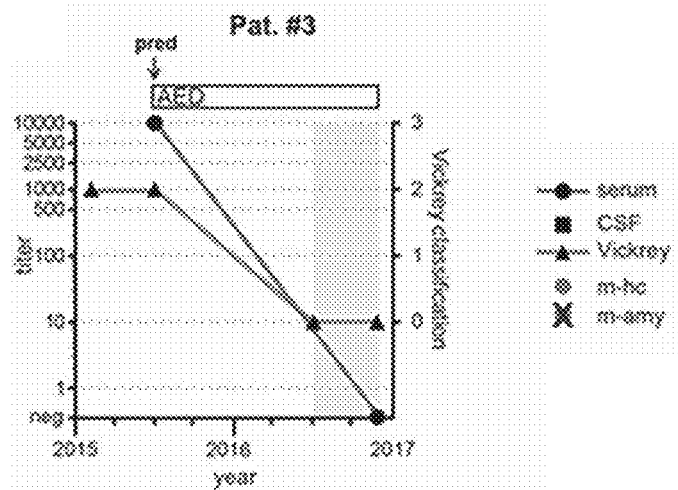
FIG. 4C shows dynamics of seizures and anti-Drebrin autoantibody titers correlated to therapeutic aspects for Patient #3. Seizure free intervals are highlighted in grey. Outcome (triangle) is reported based on Vickrey's classification: 0—seizure free, 1—aura, 2—1-10 seizures/year; 3—>10 seizures/year. Amygdala/hippocampal volume (isometric T1-sequence) is given as mean relative volume of both amygdalae/hippocampi (mamy/m-hc) in percent. AED—anti-epileptic drugs; pred—prednisolone pulse.
Figure 4D:
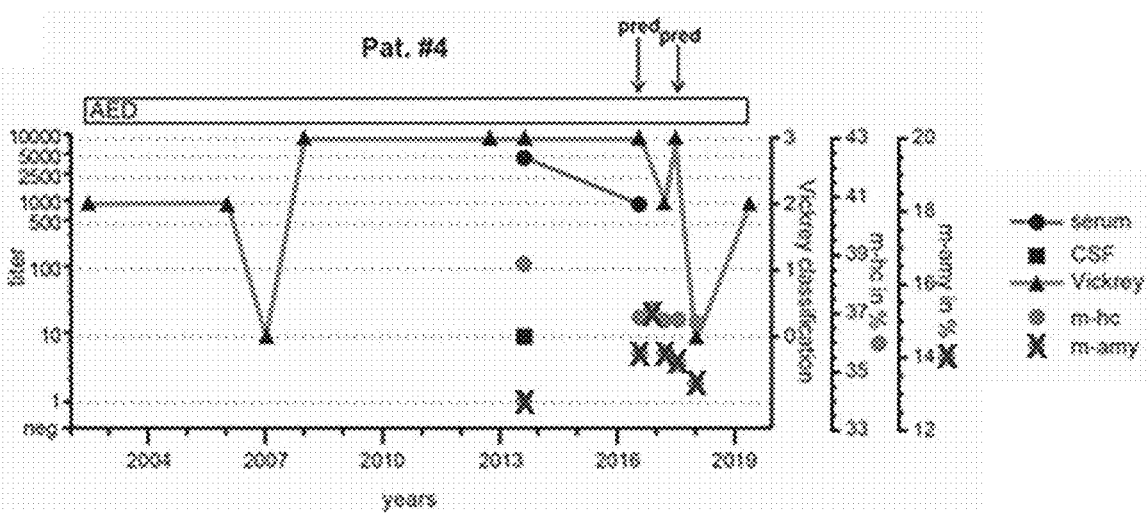
FIG. 4D shows dynamics of seizures and anti-Drebrin autoantibody titers correlated to therapeutic aspects for Patient #4. Outcome (triangle) is reported based on Vickrey's classification: 0—seizure free, 1—aura, 2—1-10 seizures/year; 3—>10 seizures/year. Amygdala/hippocampal volume (isometric T1-sequence) is given as mean relative volume of both amygdalae/hippocampi (mamy/m-hc) in percent. AED—anti-epileptic drugs; pred—prednisolone pulse.

FIGS. 3A-J show representative cMRI and neuropathological findings in anti-Drebrin AB$^+$ patients. FIGS. 3A-D. Findings on cMRI scans (T2-FLAIR (fluid attenuated inversion recovery) images) ranged from very subtle to extensive changes involving not only limbic but cortical structures. FIG. 3A. cMRI of patient #2 revealed swelling and T2-hyperintensity of the right amygdaloid area (white arrow) as well as a certain loss of the internal organoid texture of the right sided hippocampal formation (FIG. 3B, white arrow). FIG. 3C. In contrast to these circumscribed limbic changes, in patient #4 the cMRI showed extensive atrophy of the left hemisphere (white arrow) as well as some swelling of the left amygdala. FIG. 3D. Additionally, there was only a slight volume reduction of the left hippocampus (white arrow). FIG. 3E. On the HE (hematoxylin and eosin) staining in a cortical biopsy of patient #4 rather dense mononuclear infiltrates became visible with a focus in deeper cortical layers. There was substantial edema and besides lymphocytes clustering around neurons (FIG. 3E, black arrows in insert), also macrophage infiltrates were present. FIGS. 3F-G. Mononuclear infiltrates corresponded to CD3 positive T-lymphocytes (FIG. 3F, black arrow) as well as CD8 positive T-lymphoyctes clustered around blood vessel structures (FIG. 3G, arrow) and in intraparenchymal localization (FIG. 3G). FIG. 3H. Immunohistochemistry with antibodies against NeuN (neuronal nuclei) demonstrated substantial neuronal cell loss in the lower cortical layers. FIG. 3I. Concomitantly, extensive fibrillary and cellular astrogliosis was present in the GFAP immunohistochemistry. FIG. 3J. Correspondingly, immunohistochemistry with antibodies against HLA-DR demonstrated extensive activated, highly ramified microglial infiltrates as well as the presence of macrophages, some of them in perivascular localization (black arrow; bar graph corresponds to 200 μm in FIG. 3E, FIG. 3G & FIG. 3H, 50 μm in insert in FIG. 3E, 100 μm in FIG. 3F, FIG. 3I and FIG. 3J). No syndecan positive plasma cells were present (data not shown).

FIGS. 4A-D show dynamics of seizures and anti-Drebrin autoantibody titers correlated to therapeutic aspects. Patient #1 (FIG. 4A), #3 (FIG. 4C) and #4 (FIG. 4D) responded well to immunotherapy regarding serological parameters as well as seizure outcome. Amygdala and hippocampal volume accessed by serial cMRI examinations in Patient #1 and #4 decreased under immunotherapy. Patient #2 (FIG. 4B) improved clinically on AED (anti-epileptic drugs) therapy. Seizure free intervals are highlighted in grey. Outcome (triangle) is reported based on Vickrey's classification: 0—seizure free, 1—aura, 2—1-10 seizures/year; 3—>10 seizures/year. Amygdala/hippocampal volume (isometric T1-sequence) is given as mean relative volume of both amygdalae/hippocampi (mamy/m-hc) in percent. AED—anti-epileptic drugs; pred—prednisolone pulse.

Figures 5A, 5B, 5C:
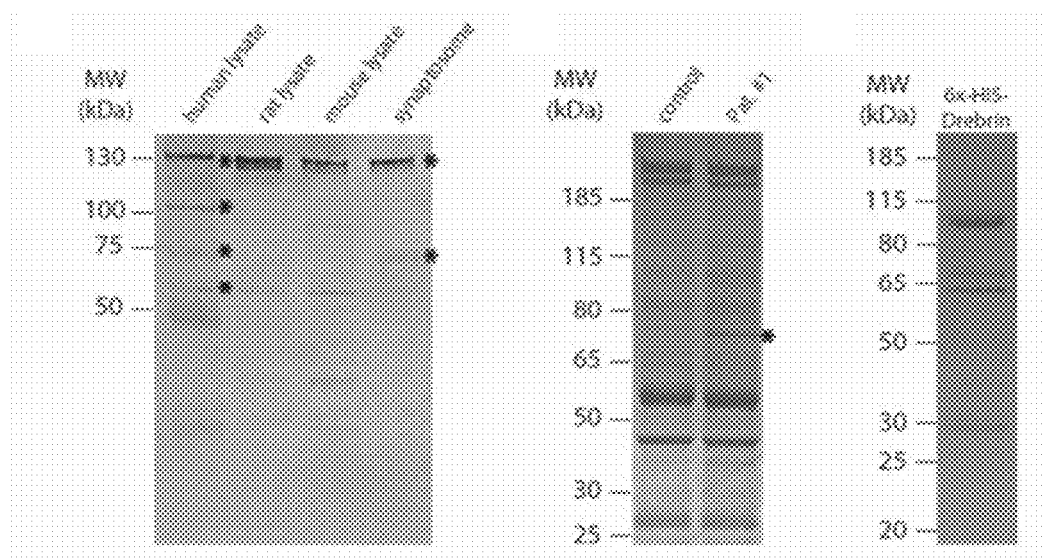
FIG. 5A shows incubation of representative patient's serum on human, rat, mouse and synaptosome fraction lysate coated blots revealed a remarkable strong band pattern (~130 kDa, ~105 kDa, ~70 kDa and ~55 kDa, asterisks).
FIG. 5B shows Coomassie stained SDS-PAGE after immunoprecipitation performed with serum of an immunoblot screening negative control and index patient (patient #1) with a band of approximately 70 kDa (asterisks) identified by MS as Drebrin.
FIG. 5C shows Coomassie stained gel of human Drebrin protein purified from bacteria. Due to the large number of negatively charged residues in the protein, the detected band size differs from the calculated molecular weight.
Figures 5D, 5E:
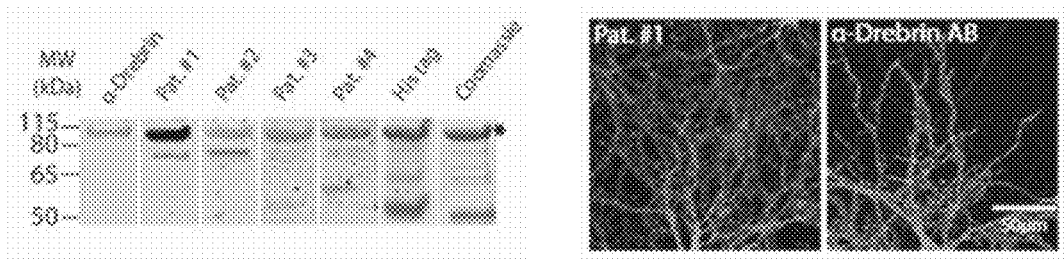
FIG. 5D shows sera of the four patients included in the present series showed reactivity with the purified human Drebrin protein (asterisk). The same band is revealed by Coomassie staining and detected with antibodies against Drebrin and the His tag.
FIG. 5E shows representative immunolabeling of human anti-Drebrin autoantibodies from index patient #1 in cultured primary hippocampal neurons compared to a mouse monoclonal anti-Drebrin antibody. Both antibodies showed a similar neuropil expression pattern with strong immunoreactivity on dendritic spines, supporting a binding to the same target protein Drebrin.
Figure 5F:
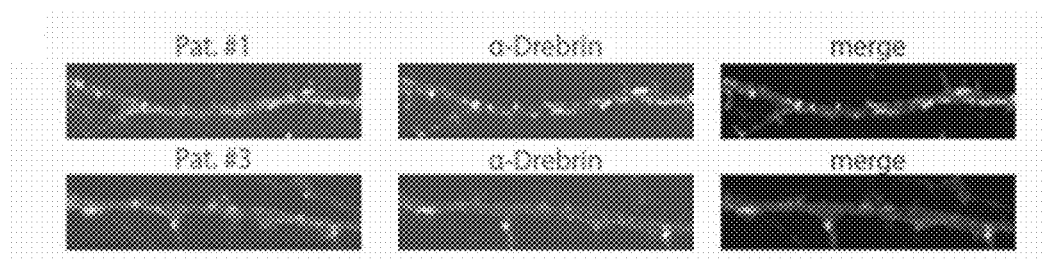
FIG. 5F shows patient serum and a mouse monoclonal anti-Drebrin antibody strongly labelled dendritic spines, in which Drebrin is enriched.
Figure 5G:
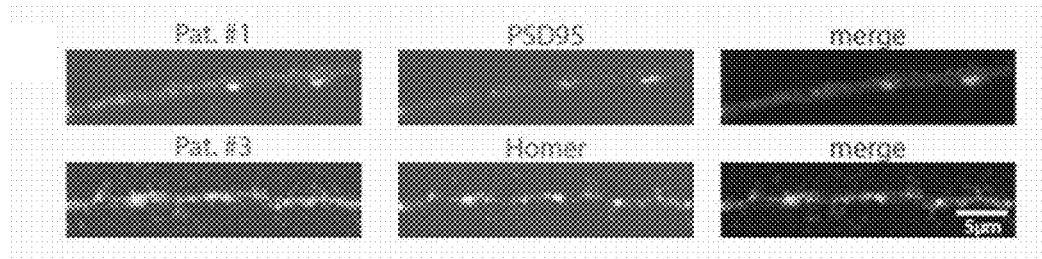
FIG. 5G shows that containing with antibodies against the postsynaptic proteins PSD95 or Homer showed a strong colocalization at dendritic spines indicating the presence of Drebrin at the excitatory postsynapse.

FIGS. 5A-G show the characterization of the anti-Drebrin autoantibody. FIG. 5A. Incubation of representative patient's serum on human, rat, mouse and synaptosome fraction lysate coated blots revealed a remarkable strong band pattern (~130 kDa, ~105 kDa, ~70 kDa and ~55 kDa, asterisks). FIG. 5B. Coomassie stained SDS-PAGE after immunoprecipitation performed with serum of an immunoblot screening negative control and index patient (patient #1) with a band of approximately 70 kDa (asterisks) identified by MS as Drebrin. FIG. 5C. Coomassie stained gel of human Drebrin protein purified from bacteria. Due to the large number of negatively charged residues in the protein, the detected band size differs from the calculated molecular weight. FIG. 5D. Sera of the four patients included in the present series showed reactivity with the purified human Drebrin protein (asterisk). The same band is revealed by Coomassie staining and detected with antibodies against Drebrin and the His tag. FIG. 5E. Representative immunolabeling of human anti-Drebrin autoantibodies from index patient #1 in cultured primary hippocampal neurons compared to a mouse monoclonal anti-Drebrin antibody. Both antibodies showed a similar neuropil expression pattern with strong immunoreactivity on dendritic spines, supporting a binding to the same target protein Drebrin. FIG. 5F. Patient serum and a mouse monoclonal anti-Drebrin antibody strongly labelled dendritic spines, in which Drebrin is enriched. FIG. 5G. Costaining with antibodies against the postsynaptic proteins PSD95 or Homer showed a strong colocalization at dendritic spines indicating the presence of Drebrin at the excitatory postsynapse.

Figure 6:
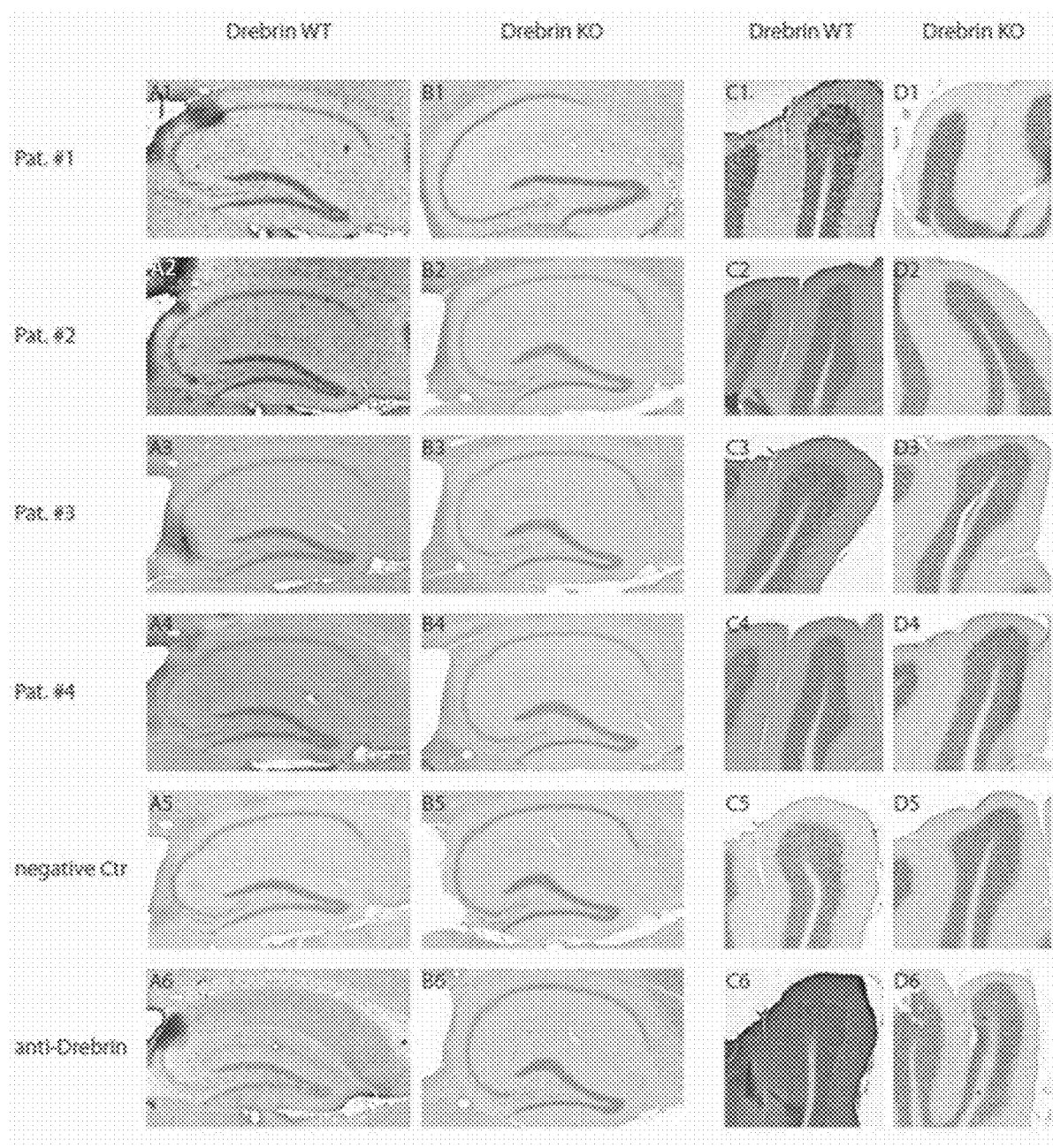
FIG. 6 shows the comparison of individual patients' sera reactivity using brain slices from Drebrin knockout versus wildtype mice.

FIG. 6 shows the comparison of individual patients' sera reactivity using brain slices from Drebrin knockout versus wildtype mice. (A1-4) Anti-Drebrin AB+ patient sera and (A6) a mouse monoclonal anti-Drebrin antibody showed a strong labelling within the hippocampal formation in wildtype mice. (B1-4) In contrast, no binding pattern was detectable on hippocampal slices in a parallel experiment using hippocampi from Drebrin knockout mice. (B6) Staining was also absent with the commercial mouse monoclonal anti-Drebrin antibody. (C1-5) Correspondingly, the present binding pattern in the cerebellar molecular layer in wildtype mice (D1-4) was abrogated in the Drebrin knockout mice (C6, D6) similar to the mouse monoclonal anti-Drebrin antibody. No staining was visible in the negative control using NHS, approximately 1500 pooled samples from healthy individuals (A5, B5, C5, D5). The delicate neuropil binding pattern in the hippocampi and the cerebellar molecular layer of wildtype mice incubated with patients' sera strongly recapitulating the pattern of mouse monoclonal anti-Drebrin antibody.

Figure 7A:
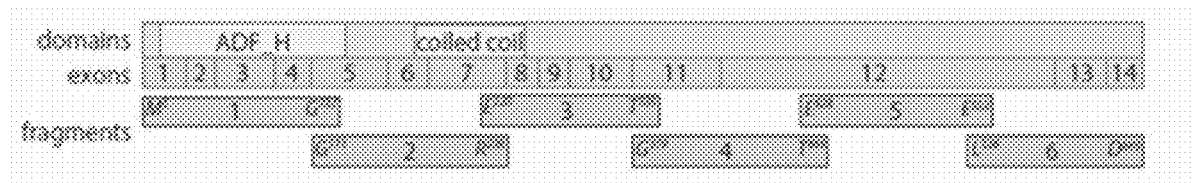
FIG. 7A shows a scheme of full-length Drebrin protein, with its domains, exons structure and the overlapping Drebrin fragments 1-6.
Figure 7B:
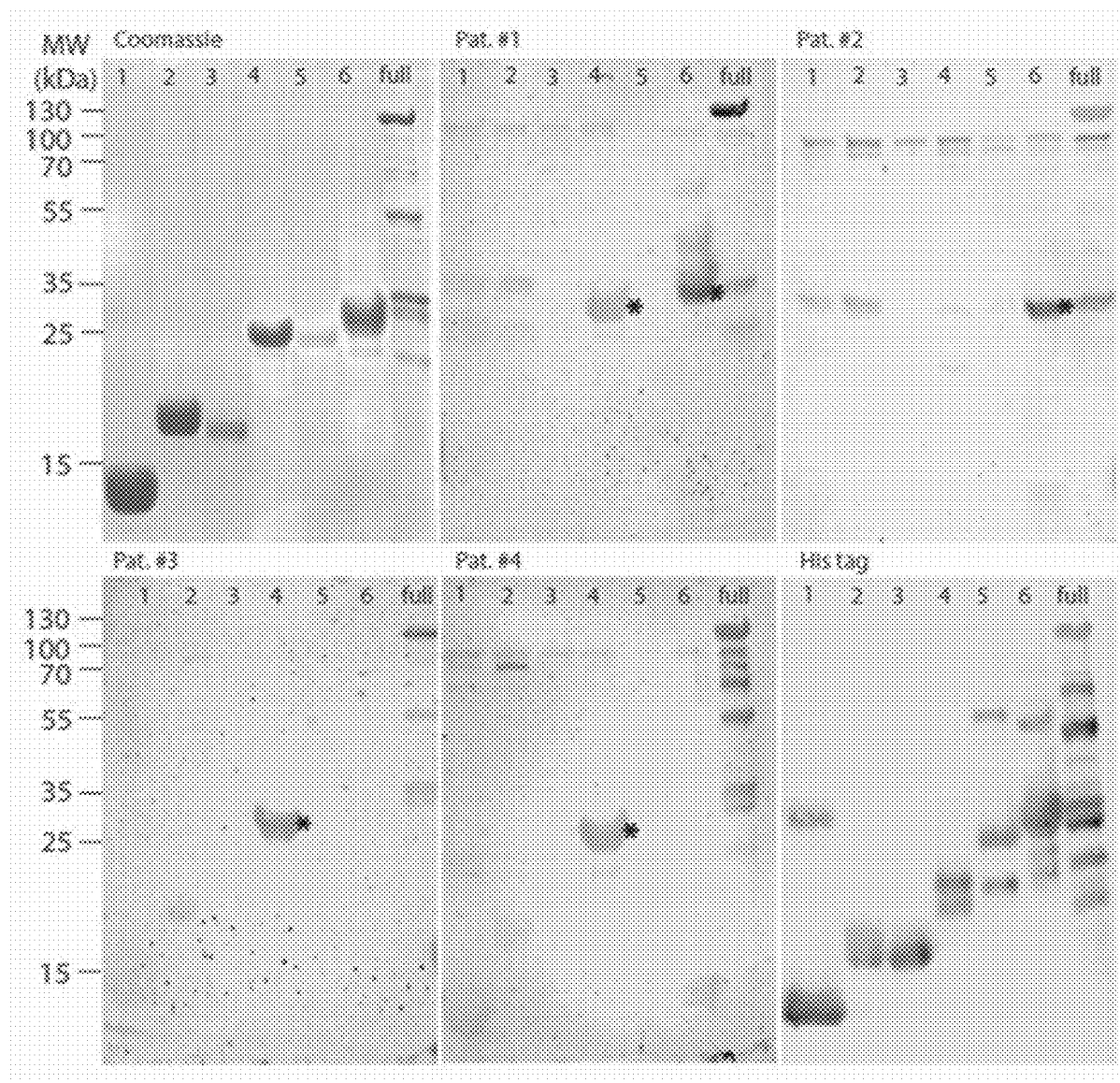
FIG. 7B shows representative immunoblots of the full-length Drebrin and its fragments 1-6 labeled with human autoantibodies from sera of patients #1-4 detected full-length Drebrin and fragments 4 and 6 (asterisks). Coomassie and anti-His tag staining shows the amount of the purified proteins loaded for immunoblotting.

FIGS. 7A-B show a binding analysis of Drebrin fragments. FIG. 7A. Scheme of full-length Drebrin protein, showing its domains, exons structure and the overlapping Drebrin fragments 1-6. FIG. 7B. Representative immunoblots of the full-length Drebrin and its fragments 1-6 labeled with human autoantibodies from sera of patients #1-4 detected full-length Drebrin and fragments 4 and 6 (asterisks). Coomassie and anti-His tag staining shows the amount of the purified proteins loaded for immunoblotting.

The present application comprises a range of sequences, more specifically:

(Fragment$_{G319-T444}$ of human Drebrin)
SEQ ID NO: 1
GSHLDSHRRMAPTPIPTRSPSDSSTASTPVAEQIERALDEVTSSQPPPLP
PPPPPAQETQEPSPILDSEETRAAAPQAWAGPMEEPPQAQAPPRGPGSPA
EDLMFMSAEQAVLAAPVEPATADAT (Fragment$_{L536-D649}$ of human Drebrin)
SEQ ID NO: 2
LPEPPATFCDPEEVEGESLAAPQTPTLPSALEELEQEQEPEPHLLTNGET
TQKEGTQASEGYFSQSQEEEFAQSEELCAKAPPPVFYNKPPEIDITCWDA
DPVPEEEEGFEGGD (human Drebrin E)
SEQ ID NO: 3
MAGVSFSGHRLELLAAYEEVIREESAADWALYTYEDGSDDLKLAASGEGG
LQELSGFIFENQKVMYGFCSVKDSQAALPKYVLINWVGEDVPDARKCACA
SHVAKVAEFFQGVDVIVNASSVEDIDAGAIGQRLSNGLARLSSPVLHRLR
LREDENAEPVGTTYQKTDAAVEMKRINREQFWEQAKKEEELRKEEERKKA
LDERLRFEQERMEQERQEQEERERRYREREQQIEEHRRKQQTLEAEEAKR
RLKEQSIFGDHRDEEEETHMKKSESEVEEAAAIIAQRPDNPREFFKQQER
VASASAGSCDVPSPFNHRPGSHLDSHRRMAPTPIPTRSPSDSSTASTPVA
EQIERALDEVTSSQPPPLPPPPPAQETQEPSPILDSEETRAAAPQAWAG
PMEEPPQAQAPPRGPGSPAEDLMFMESAEQAVLAAPVEPATADATEIHDA
ADTIETDTATADTTVANNVPPAATSLIDLWPGNGEGASTLQGEPRAPTPP
SGTEVTLAEVPLLDEVAPEPLLPAGEGCATLLNFDELPEPPATFCDPEEV
EGESLAAPQTPTLPSALEELEQEQEPEPHLLTNGETTQKEGTQASEGYFS
QSQEEEFAQSEELCAKAPPPVFYNKPPEIDITCWDADPVPEEEEGFEGGD (human Drebrin A)
SEQ ID NO: 4
MAGYSFSGHRLELLAAYEEVIREESAADWALYTYEDGSDDLKLAASGEGG
LQELSGHFENQKVMYGFCSVKDSQAALPKYVLINWVGEDVPDARKCACAS
HVAKVAEFFQGVDVIVNASSVEDIDAGAIGQRLSNGLARLSSPVLHRLRL
REDENAEPVGTTYQKTDAAVEMKRINREQFWEQAKKEEELRKEEERKKAL
DERLRFEQERMEQERQEQEERERRYREREQQIEEHRRKQQTLEAEEAKRR
LKEQSIFGDHRDEEEETHMKKSESEVEEAAAIIAQRPDNPREFFKQQERV
ASASAGSCDVPSPFNHRPGRPYCPFIKASDSGPSSSSSSSSSPPRTPFPY
ITCHRTPNLSSSLPCSHLDSHRRMAPTPIPTRSPSDSSTASTPVAEQIER
ALDEVTSSQPPPLPPPPPAQETQEPSPILDSEETRAAAPQAWAGPMEEP
PQAQAPPRGPGSPAEDLMFMESAEQAVLAAPVEPATADATEIHDAADTIE
TDTATADTTVANNVPPAATSLIDLWPGNGEGASTLQGEPRAPTPPSGTEV
TLAEVPLLDEVAPEPLLPAGEGCATLLNFDELPEPPATFCDPEEVEGESL
AAPQTPTLPSALEELEQEQEPEPHLLTNGETTQKEGTQASEGYFSQSQEE
EFAQSEELCAKAPPPVFYNKPPEIDITCWDADPVPEEEEGFEGGD The present invention is further illustrated by the following non-limiting examples from which further features, embodiments, aspects and advantages of the present invention may be taken.

Examples

Summary

Methods: Sera of four patients with adult onset epilepsy and suspected chronic encephalitis of unresolved etiology and corresponding results in immunoblot-based autoantibody screening were subjected to target identification. Therefore, immunoblotting was followed by immunoprecipitation and mass-spectrometry, subcellular binding pattern analyses in primary neuronal cultures and immunohistochemistry in brains of wildtype and Drebrin knockout mice.

Results: In a patient with adult onset epilepsy and suspected encephalitis, immunoblot band at ~70 kDa were detected, for which immunoprecipitation and mass spectrometry revealed Drebrin as putative antigen. Three other patients with an equivalent immunoblot result were also anti-Drebrin autoantibody positive. These autoantibodies were not detected in 1500 pooled normal human serum samples. In addition to seizures, memory impairment and increased protein content in cerebrospinal fluid, rheumatic symptoms and leukemia occurred in anti-Drebrin autoantibody positive patients. Alterations in cerebral magnetic resonance imaging comprised amygdalo-hippocampal T2-signal increase but also hippocampal sclerosis. Diagnostic biopsy revealed cytotoxic T-lymphocytic encephalitis in one anti-Drebrin autoantibody positive patient. Anti-Drebrin autoantibody titer, seizures as well as neuropsychiatric symptoms responded to immunosuppressant therapy and relapsed when tapering immunotherapy.

Patients

Probes of four patients with neuropsychiatric symptoms including recurrent seizures and impairment of cognition and behavior revealed in immunoblot screening a prominent band around 70 kDa. In none of the four patients common 'neurological' autoantibodies using commercial kits for diagnostic procedures were detected. All procedures were conducted in accordance with the Declaration of Helsinki. Informed written consent was obtained from every patient.

Clinical data of all four patients is summarized in FIGS. 1, 2 and 4A-D.

Screening Tests for Novel Autoantibodies

Screening tests for potential novel autoantibodies comprise immunoblotting and indirect immunofluorescence test (IIFT). For immunoblots, protein lysates of rat and mouse brain, of human hippocampal tissue from pharmacoresistant temporal lobe epilepsy patients undergoing epilepsy surgery for seizure relief and of murine crude synaptosomes were isolated, separated by electrophoresis and blotted. After blocking with (2% (w/v) bovine serum albumin (BSA), 2% (w/v) fetal calf serum (FCS), 0.2% (w/v) cold water fish gelatin in phosphate-buffered saline (PBS), proteins were incubated with serum (1:500) and CSF (1:100) in a total volume of 7 ml overnight, washed with PBS/Tween 20, incubated with goat anti-human IRDye 800CW (Odyssey, 926-32232) for 45 min, and imaged with the Odyssey Imaging System (LI-COR) after another washing step.

For IIFT screening, a custom-made biochip-based-assay (IIFT: Neurologie-Mosaik28, Euroimmun, FA 111-1005-28) was used including rat and simiiform slices of cerebellum and hippocampus in order to screen for binding patterns of autoantibodies in sera and CSF of LE patients (dilution: serum 1:10, CSF 1:1). All IIFT-assays were analyzed by an expert examiner (AJB).

Immunoprecipitation and Mass-Spectrometry 1 g of freshly dissected rat brain tissue was homogenized in 5 ml buffer (100 mmol/L Tris(hydroxymethyl)-aminomethan (Tris)-HCl pH 6.5, 150 mmol/L sodium chloride, 1 mmol/L ethylenediaminetetraacetate (EDTA), 1% (w/v) sodium deoxycholate, and 1% (w/v) Triton X-100, 1% (w/v) N-octyl-beta-D-glucopyranoside) containing protease inhibitors. Lysate was rotated 3 h at 4° C. and centrifuged at 21000×g for 15 min at 4° C. The clear supernatant was incubated with biomaterial for 3 h at 4° C. before adding Protein G Dynabeads (Thermo Fisher Scientific) and incubation overnight. Beads were washed three times using buffer as outlined above. Elution was performed at 70° C. for 10 min using NuPAGE LDS sample buffer (Thermo Fisher Scientific) containing 25 mmol/L dithiothreitol. Prior to 4-12% SDS-PAGE (NuPAGE system, Thermo Fisher Scientific) carbamidomethylation was performed. Proteins were visualized with Roti-Blue Solution (Roth). Additional bands compared to patterns observed with serum/CSF from healthy controls were excised from the gel, destained and dehydrated with 50% and 100% w/v acetonitrile. Proteins were digested by 0.4 µg trypsin at 37° C. for 6 h. To extract the peptides 100 µl acetonitrile in increasing concentration (50%, 100% w/v) was added, incubated for 5 min and the supernatant was collected. Peptides were lyophilized and transferred to the mass-spectrometry (MS) for protein identification.

Cloning of Drebrin Fragments

The full-length human Drebrin cDNA sequence was divided into 6 fragments of similar length with 51 bp overlap at both ends of the fragments. Drebrin fragments 1-6 were cloned into pETDuet1-T7-His-hDrebrin (wt) (Addgene plasmid #4036224) by replacement of the full-length Drebrin via EcoRI/NotI restriction sites. Plasmids were verified by sequencing.

Validation of Anti-Drebrin Autoantibody Binding

Recombinant human Drebrin protein and Drebrin fragments 1-6 were purified by $Ni^+$-affinity purification following the Qiagen protocol. Therefore, a pETDuet1-T7-His-hDrebrin (wt) plasmid (Addgene plasmid #4036224) and the newly generated pETDuet1-T7-His-Drebrin fragments 1-6 were transformed into competent BL21 E. coli cells. Protein expression was induced by addition of 1 mM IPTG (isopropyl β-D-1 thiogalactopyranoside) and cells were lysed in lysis buffer (50 mmol/l sodium phosphate, 300 mmol/l sodium chloride, 5 mmol/l Imidazol, pH 8.0) by sonification. After centrifugation of the lysate the supernatant was incubated for 1 h with $Ni^+$-nitrilotriacetic acid (NTA)-Agarose (Qiagen). $Ni^+$-NTAAgarose was washed with wash buffer containing increasing imidazole concentrations (5-80 mmol/l imidazole, 50 mmol/I sodium phosphate, 300 mmol/l sodium chloride, pH 8.0). The protein was eluted three times with 250 mmol/l imidazole solution for 30 min. 800 ng of the protein was loaded on a SDS-PAGE and either stained with Coomassie or blotted and blocked as described above. The membrane was transferred to a Mini-PROTEAN II Multiscreen Apparatus (Bio-Rad) and incubated with different biomaterial (all four anti-Drebrin autoantibody positive patients, normal human serum (NHS); dilution: Serum 1:100; CSF 1:1) and commercial anti-Drebrin (ab12350, abcam, 1:200) and anti-His tag (ab18184, abcam, 1:1000) antibodies in blocking buffer overnight. Bands were visualized as described above using goat anti-mouse and goat anti-human IRDye 800CW (926-32210, 926-32232, Odyssey) secondary antibodies.

Immunocytochemistry on Primary Neuronal Cells

Primary cultured mouse hippocampal neurons were prepared and fixed with 4% paraformaldehyde (PFA) in PBS for 15 min, followed by three washing steps in PBS. Cells were permeabilized with PBS/Tween 20 (0.3% (w/v) Triton X-100) for 10 min. Neurons were incubated overnight with primary antibodies (anti-Drebrin, ab12350, abcam, 1:1000; anti-PSD95, 75-028, neuromab, 1:500; anti-Homer, 160004, synaptic system, 1:1000), or serum (1:200) of respective patients in PBS/Tween 20 (0.1% (w/v) Triton X-100) at 4° C. After three PBS washing steps Alexa Fluor® secondary antibodies (goat anti-human A11013, Invitrogen; goat anti-mouse A11001, Invitrogen 1:1000; goat anti-guinea pig A11-073, Invitrogen 1:1000) and 4',6-Diamidin-2-phenylindol (DAPI 1:100) in PBS/Tween 20 were incubated for 45 min. Before mounting with Mowiol® cells were washed again three times. Images were taken using a confocal microscope (Nikon Eclipse Ti confocal microscope, Nikon Instruments).

Immunohistochemistry with Wildtype and Drebrin Knockout Mice

Adult male Drebrin knockout (Jung G et al. J Neurochem. 2015; 134:327-39) and age matched wildtype mice were sacrificed under deep isoflurane anesthesia. Brains were quickly removed and fixed in 4% PFA for 1 hour at 4° C., incubated in 40% sucrose for another 24 h and snap frozen in isopentane chilled with liquid nitrogen. 18 µm thick cryosections were air-dried and sequentially incubated with 3% $H_2O_2$ and 0.5% Triton X-100 for 20 min, 10% goat serum for 1 h, and patient or control serum (1:200) or a monoclonal mouse anti-Drebrin antibody (ab12350, abcam, 1:1000) at 4° C. overnight. After using the appropriate secondary biotinylated antibodies (Life technologies, 1:500), the reactivity was examined with standard avidin-biotin-peroxidase method.

Neuropathology

Biopsy brain tissue of one retrospectively anti-Drebrin autoantibody positive patient was neurosurgically removed for diagnostic purposes. As described before, tissue was fixed in PFA overnight and embedded in paraffin. Deparaffinized 4.0 µm sections were stained with hematoxylin and eosin (HE) and commercial antibodies specific for cluster of differentiation 3 (CD3), cluster of differentiation 8 (CD8), (neuronal nuclei (NeuN), glial fibrillary acidic protein (GFAP) and (human leukocyte antigen-DR isotype (HLA-DR). Staining was visualized using the avidinbiotin-peroxidase method.

Neuroimaging

Patients underwent cMRI in two different systems. A 3D T1-weighted sequence was acquired on an Achieva 3.0T TX (Philips Healthcare Best, The Netherlands) with the following parameters: voxel size=1×1×1 mm$^3$, TR=8.1 ms, TE=3.7 ms, flip angle=8°, matrix=256×256 pixel. A T1-weighted magnetization prepared rapid acquisition gradient echo sequence (MPRAGE) was acquired on a 3T Siemens MAGNETOM Trio (Siemens Healthineers, Erlangen, Germany) using a 32-channel head coil: voxel size=0.8×0.8×0.8 mm$^3$, TR=1660 ms, TE=2.54 ms, flip angle=9°, matrix=320×320 pixel. Volumetric analysis of the amygdala, the hippocampus, and intracranial volume was carried out using the Freesurfer v6.0.0 image analysis suite. Parcellation results were visually checked for accuracy and alignment by two independent raters. All analyzed volumes were adjusted by the intracranial volume minus the ventricular volume.

Controls

NHS (approx. 1500 pooled samples from healthy individuals) was used as control.

Example 1: Clinical Diagnosis and Therapeutic Treatment of Patients #1-4

All four patients positively tested for anti-Drebrin autoantibody (anti-Drebrin AB$^+$; 1 male, 3 females; age at onset 45, range 23-68 years) developed a subacute progressive encephalopathy with the major symptoms of neuropsychiatric impairment involving depression and cognitive impairment and/or confirmed or clinically suspected focal epileptic seizures or status epilepticus (FIG. 1). CSF alterations comprised increased protein levels in all patients as well as mononuclear cell pleocytosis in at least one individual. cMRI alterations in T2-weighted images included dynamic hippocampal volume changes as well as extrahippocampal atrophy (representative cMRI imaging of patient #2 in FIGS. 3A to 3D). Cerebral brain tissue for neuropathological analysis was available for one of these cases (patient #4) using a diagnostic brain biopsy 10 years after disease onset which revealed a T-lymphocytic driven neurodegenerative encephalitis (FIGS. 3E to 3J). In three patients (patient #1-3), individual immunotherapy led to a clinical improvement with respect to seizure control as well as autoantibody titer decrease and/or neuropsychological performance (FIGS. 2 and 4A-D). The index patient (patient #1) had a neuropil binding pattern on rodent and simiiform hippocampal slices as well as a remarkable reactivity on an immunoblot with several bands including bands at ~55 kDa, ~70 kDa, ~100 kDa and ~130 kDa in all brain protein lysates as well as synaptosome lysate (FIG. 5A, asterisks) that was absent in all used controls. This observation suggested the presence of antibodies others than common neurological autoantibodies, which had been ruled out previously in this serum sample.

Example 2: Identification of the Target Antigen Drebrin

Following the IP of rat brain lysate with antibodies isolated from the serum of the index patient (patient #1) the Coomassie stained SDS-PAGE also showed an additional 70 kDa band (FIG. 5B, asterisk), which was not present in any of the controls. MS of this band identified Drebrin (molecular weight: 71 kDa) as the most abundant protein present in the excised gel piece in multiple independent experiments. The detection of multiple bands in the immunoblot screening of brain and synaptosome homogenates in the present patient series (FIG. 5A) could be due to protein degradation, complex post-translational modification of Drebrin or the presence of low amounts of additional so far unresolved autoantibodies.

To establish a screening assay, polyhistidine-(6×-His)-tagged recombinant human Drebrin protein from bacteria was purified for immunoblotting experiments with patient sera (FIG. 5C). Immunoblotting with the serum of the index patient (patient #1) showed a band at the expected size ~90 kDa (FIG. 5D). Drebrin has been reported to run higher than its calculated mass in SDS-PAGE due to strong negative charge of the protein. Next, we screened the serum of all four patients—patient #1 and three additional patients with equivalent results in the initial immunoblot screening of brain and synaptosome homogenates—as well as a mouse monoclonal anti-Drebrin antibody, as positive control. We observed reactivity at ~90 kDa (FIG. 5D). The titer in the four patients' serum ranged from 1:1000 to 1:10000, in three patients anti-Drebrin autoantibodies were also detected in corresponding CSF samples with a titer ranging from 1:1 to 1:100. NHS control (approx. 1500 pooled samples from healthy individuals) did not show any reactivity to the recombinant Drebrin protein.

Example 3: Analysis of the Patients' Biomaterial Reactivity in Cultured Hippocampal Neurons The serum of all four patients showed delicate dendritic reactivity on permeabilized cultured mouse primary hippocampal neurons reflecting the pattern of the mouse monoclonal anti-Drebrin antibody (representative stainings in FIG. 5E). Binding pattern in cultured neurons revealed reactivity towards the neuropil, especially at dendritic spines and were similar compared to the pattern of a commercial monoclonal anti-Drebrin antibody (representative stainings in FIG. 5F). All patients' anti-Drebrin autoantibodies showed colocalization with postsynaptic density protein 95 (PSD95) and Homer at the excitatory postsynaptic density (representative stainings in FIG. 5G).

Example 4: Validation of Anti-Drebrin Autoantibodies in Drebrin Knockout Mice

In order to verify the presence of anti-Drebrin autoantibodies in the patients' biomaterial brain slices from Drebrin knockout and age matched wildtype mice, said slices were exposed to anti-Drebrin AB+ patients' sera. The sera of all four patients (FIG. 6, A1-4), as well as the commercial anti-Drebrin antibody (FIG. 6, A6) showed strong reactivity on wildtype mice slices with an increased binding in the hippocampal formation and the cerebellar molecular layer (FIG. 6, C1-4,6). This pattern was completely absent in the tissue of knockout mice (FIG. 6, B1-4,6, D1-4,6) and within the negative control (FIG. 6, A5, C5).

Example 5: Characterization of the Drebrin Autoantibody Binding Region in all Four Patients In order to find regions of Drebrin binding to the autoantibodies, the Drebrin protein coding sequence was divided into 6 fragments that are 113-127 aa long and have 17 aa overlapping regions on both ends (FIG. 7A). Drebrin fragments 1-6 were purified via the His tag and analyzed by SDS-PAGE (FIG. 7B). Coomassie and anti-His tag labeling of the proteins showed that fragments 4-6 run higher and fragment 1 lower than expected, probably due to their stronger negative and positive charge, respectively, which also explains that full-length Drebrin appears on a SDS-PAGE at a higher molecular weight than calculated. Immunoblots with the serum of patient #1 showed a strong reaction with Drebrin fragment 6 and a weaker interaction with fragment 4. The same fragments were detected when biomaterial of other patients was used.

Fragment 4 was stained by sera of patients #3 and 4, fragment 6 was detected by serum of patient #2. Fragments 1-3 and 5 didn't show a reaction with any patients' sera (FIG. 7B).

All documents cited herein, are hereby incorporated by reference in their entirety.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A method, comprising:
   detecting in a sample of a patient having or suspected of having a neurological disease the presence of an autoantibody specifically binding to Drebrin.

2. The method according to claim 1, wherein the neurological disease is a neurological autoimmune disease.

3. The method according to claim 2, wherein the neurological autoimmune disease is autoimmune encephalitis, seizure disorder, or epilepsy.

4. The method according to claim 1, wherein the sample is blood, serum, plasma, cerebrospinal fluid (CSF), urine, or saliva.

5. The method according to claim 1, wherein the autoantibody is selected from the group consisting of IgG, IgA, and IgM class antibodies.

6. The method according to claim 1, wherein the detection comprises
   a blot assay, chemiluminescence immunoassay, enzyme-linked immunosorbent assay (ELISA), light scattering immunoassay, radiolabeled immunoassay, or immunofluorescence assay.

7. A method of detecting the presence or absence of an autoantibody specifically binding to Drebrin, the method comprising:
   i) contacting a sample isolated from a subject having a neurological disease with a peptide comprising SEQ ID NO: 1, SEQ ID NO: 2, SEQ ID NO: 3, or SEQ ID NO: 4, wherein the peptide binds specifically to autoantibodies binding to SEQ ID NO: 1, SEQ ID NO: 2, SEQ ID NO: 3, or SEQ ID NO: 4; and
   ii) detecting the presence or absence of the autoantibody against Drebrin in a complex with the peptide.

* * * * *

UNITED STATES PATENT AND TRADEMARK OFFICE
CERTIFICATE OF CORRECTION

| | |
|---|---|
| PATENT NO. | : 11,644,463 B2 |
| APPLICATION NO. | : 16/947631 |
| DATED | : May 9, 2023 |
| INVENTOR(S) | : Susanne Schoch McGovern and Albert Becker |

It is certified that error appears in the above-identified patent and that said Letters Patent is hereby corrected as shown below:

In the Claims

Column 39, Line 3, in Claim 1 currently reads "detecting in a sample of a patient haying or suspected of" and should read --"detecting in a sample of a patient having or suspected of--.

Signed and Sealed this
Fifth Day of September, 2023

Katherine Kelly Vidal
*Director of the United States Patent and Trademark Office*